(12) United States Patent
Lam et al.

(10) Patent No.: US 6,689,567 B1
(45) Date of Patent: Feb. 10, 2004

(54) METHOD FOR ASSAYING THE FUNCTION OF FLAA1 AND WBPM

(75) Inventors: Joseph S. Lam, Guelph (CA); Carole Creuzenet, Guelph (CA); Lori L. Burrows, Oakville (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 09/578,515

(22) Filed: May 26, 2000

Related U.S. Application Data

(60) Provisional application No. 60/136,564, filed on May 28, 1999.

(51) Int. Cl.[7] .................. G01N 35/53; C12Q 1/527; C12N 9/88
(52) U.S. Cl. .................. 435/7.1; 435/4; 435/232
(58) Field of Search .................. 435/232, 7.1, 4

(56) References Cited

U.S. PATENT DOCUMENTS 6,582,910 B1 * 6/2003 Lam et al. .................. 435/6

OTHER PUBLICATIONS

Burrows et al., "Functional Conservation of the Polysaccharide Biosynthetic Protein WbpM and Its Homologues in Pseudomonas aeruginosa and Other Medically Significant Bacteria" (2000) Infect. Immun. 68(2), 931–936.*

Creuzenet et al., "FlaA1, a New Biofunctional UDP–GlcNAc C6 Dehydratase/C4 Reductase from Helicobacter pylori" (2000) J. Biol. Chem., 275(45), 34873–34880.*

Creuzenet et al., "Structure Function Studies of Two Novel UDP–GlcNAc C6 Dehydratase/C4 Reductases" (2002) J. Biol. Chem., 277(30), 26769–26778.*

IUBMB Enzyme Nomenclature, "EC 4.2.1.76", accessed on Internet on, Sep. 23, 2003 at www.chem.qmul.ac.uk/iubmb/.*

* cited by examiner

*Primary Examiner*—Jon P. Weber
(74) *Attorney, Agent, or Firm*—Bereskin & Parr

(57) ABSTRACT

Methods for detecting FlaA1 and enzymes with FlaA1-like activity are disclosed. Methods for screening for inhibitors of the enzymes are disclosed which are useful as antimicrobial agents.

8 Claims, 17 Drawing Sheets

FIGURE 2

```
...1 atgcaccacc accaccacca cggttccatg tcaatgccaa atcatcaaaa
..51 catgctagac aaccaaacga ttttaatcac cggtggcact gggagttttg
.101 gcaaatgctt tgttcgtaaa gttttagaca ccaccaacgc taaaaaaatc
.151 atcgttata gccgagatga attgaaacaa agcgaaatgg ccatggaatt
.201 taatgatcct agaatgcgtt ttttatcgg cgatgtcagg gatttagagc
.251 gcttgaatta cgcttagag ggcgtggata tttgtatcca tgcggccgcg
.301 ctcaagcatg tccctatcgc tgaatacaac cccctagaat gcattaaaac
.351 taacattatg ggagcgagca atgtgattaa cgcatgctta aaaacgcta
.401 tcagtcaggt tatcgctcta agcaccgata aagccgctaa cccattaac
.451 ctctacggtg caaccaaatt gtgcagcgac aagctctttg tgagtgcaaa
.501 caactttaaa ggctcttctc aaacgcaatt tagcgtggtg cgttatggta
.551 atgtggtggg gagtcgtggg agcgtggtgc cgttttttaa aaaattagtc
.601 caaaacaaag cgagtgaaat ccccattacc gatattcgca tgacacgatt
.651 ttggatcacc ttagatgagg gggtttcttt tgtgcttaaa agcttgaaaa
.701 gaatgcatgg ggggaaatt tttgtgccta aaatccctag catgaaaatg
.751 actgatctcg ccaaagccct agccctaat accctacta aaatcatagg
.801 gattcgtccg ggcgaaaaac tccatgaagt gatgatccct aaagatgaaa
.851 gccatttagc cctagaattc gaagactttt tcatcattca gccaccata
.901 agcttccaaa cgcctaaaga ttacacgctc accaaactcc atgaaaagg
.951 ccaaaaagtc gcccctgatt ttgaatacag cagccataat aacaaccaat
1001 ggctagagcc tgatgatttg ttgaaattat tatga
```

FIGURE 3

```
  1 MHHHHHGSM SMPNHQNMLD NQTILITGGT GSFCKCFVRK VLDTTNAKKI
 51 TVYSRDELKQ SEMAMEFNDP RMRFFIGDVR DLERLNYALE GVDICIHAAA
101 LKHVPIAEYN PLFCIKTNIM GASNVINACL KNAISQVIAL STDKAANPIN
151 LYGATKLCSD KLFVSANNFK GSSQTQFSVV RYGNVVGSRG SVVPFFKKLV
201 QNKASEIPIT DIRMTRFWIT LDEGVSFVLK SLKRMIGGEI FVPKIPSMKM
251 TDLAKALAPN TPTKIIGIRP GEKLHEVMIP KDESHLALEF EDFFIIQPTI
301 SFQTPKDYTL TKLHEKGQKV APDFFYSSHN NNQWLEPDDL LKLL
```

FIGURE 11

```
   1 atgcaccacc accaccacca cggttccatg ggcatgttgg ataatttgag
  51 gataaagctc ctggattgc cgcgccgcta taagcgaatg ctgcaagtcg
 101 ctgccgatgt gactcttgtg tggctatccc tctggctggc ttcttggtc
 151 aggttgggca cagaagacat gatcagcccg tttagcggcc atgctggct
 201 gttcatcgcc gcccgttgg tggccattcc cctgttcatc cgcttcggca
 251 tgtaccgggc ggtgatgcgc tacctgggca acgacgccct tatcgcgatc
 301 gccaaggccg tcaccattc cgcgctggtc ctgtcgttgc tggtctactg
 351 gtaccgctcc ccgccggcgg tggtgccgcg ttccctggtg ttcaactact
 401 ggtggttgag catgctgctg atcggcggct gcgtctggc catgcgccag
 451 tatttcatgg gagactggta ctctgctgtg cagtcggtac catttctcaa
 501 ccgccaggat ggcctgccca gggtggctat ctatggcgcg ggggcggccg
 551 ccaaccagtt ggttgcggca ttgcgtctcg gtcgggcgat ccgtccggtg
 601 gcgttcatcg atgatgacaa gcagatcgcc aaccgggtca tcgccggtct
 651 gcgggtctat accgccaagc atatccgcca gatgatcgac gagacgggcg
 701 cgcaggaggt tctcctggcg attccttccg ccactcgggc ccggcgccga
 751 gagattctcg agtccctgga gccgttcccg ctgcacgtgc gcagcatgcc
 801 cggcttcatg gacctgacca gcggccgggt caaggtggac gacctgcagg
 851 aggtggacat cgctgacctg ctgggcgcg acagcgtcgc accgcgcaag
 901 gagctgctgg aacgttgcat ccgcggtcag gtggtgatgg tgaccgggc
 951 gggcggctct atcggttcgg aactctgtcg gcagatcatg agttgttcgc
1001 ctagcgtgct gatcctgttc gagcacagcg aatacaacct ctatagcatc
1051 catcaggaac tggagcgtcg gatcaagcgc gagtcgcttt cggtgaacct
1101 gttgccgatc ctcggttcgg tgcgcaatcc cgagcgcctg gtggacgtga
1151 tgcgtacctg gaaggtcaat accgtctacc atgcggcggc ctacaagcat
1201 gtgccgatcg tcgagcacaa catcgccgag ggcgttctca acaacgtgat
1251 aggcaccttg catgcggtgc aggccgcggt gcaggtcggc gtgcagaact
1301 tcgtgctgat ttccaccgac aaggcggtgc gaccgaccaa tgtgatgggc
1351 agcaccaagc gcctggcgga gatggtcctt caggcgctca gcaacgaatc
1401 ggcaccgttg ctgttcggcg atcggaagga cgtgcatcac gtcaacaaga
1451 cccgtttcac aatggtccgc ttcggcaacg tcctcggttc gtccggttcg
1501 gtcattccgc tgttccgcga gcagatcaag cgcggcggcc cggtgacggt
1551 cacccaccog agcatcaccc gttacttcat gaccattccc gaggcagcgc
1601 agttggtcat ccaggccggt tcgatggggc agggcggaga tgtattcgtg
1651 ctggacatgg ggccgccggt gaagatcctg gagctgccg agaagatgat
1701 ccacctgtcc ggcctgagcg tgcttccga gcttcgcc catgctgaca
1751 tcgccatcga gttcagtggc ctgcgtcctg gcgagaagct ctacgaagag
1801 ctgctgatcg gtgacaacgt gaatcccacc gaccatccga tgatcatgcg
1851 ggccaacgag gaacacctga gctgggaggc cttcaaggtc gtgctggagc
1901 agttgctggc cgccgtggag aaggacgact actcgcgggt tcgccagttg
1951 ctgcgggaaa ccgtcagcgg ctatgcgcct gacggtgaaa tcgtcgactg
2001 gatctatcgc cagaggcggc gagaaccctg a
```

FIGURE 12

```
  1  MHHHHHHGSM GMLDNLRIKL LGLPRRYKRM LQVAADVTLV WLSLWLAFLV
 51  RLGTEDMISP FSGHAWLFIA APLVAIPLFI RFGMYRAVMR YLGNDALIAI
101  AKAVTISALV LSLLVYWYRS PPAVVPRSLV FNYWWLSMLL IGGLRLAMRQ
151  YFMGDWYSAV QSVPFLNRQD CLPRVAIYGA GAAANQLVAA LRLGRAMRPV
201  AFIDDDKQIA NRVIAGLRVY TAKHIRQMID ETCAQEVLLA IPSATRARRR
251  EILESLEPFP LHVRSMPGFM DLTSGRVKVD DLQEVDIADI LGRDSVAPRK
301  ELLERCIRGQ VVMVTGAGGS IGSELCRQIM SCSPSVLILF EHSEYNDYSI
351  HQELERRIKR ESLSVNLLPI LGSVRNPERL VDVMRTWKVN TVYHAAAYKH
401  VPIVFHNIAE GVLNNVIGTL HAVQAAVQVG VQNFVLISTD KAVRPTNVMG
451  STKRLAEMVL QALSNESAPL LFGDRKDVHH VNKTRFTMVR FGNVLGSSGS
501  VIPLFREQIK RGGPVTVTHP STTRYFMTIP EAAQLVIQAG SMGQGGDVFV
551  LDMGPPVKIL ELAEKMIHLS GLSVRSERSP HGDIATEFSG LRPGEKLYEE
601  LLIGDNVNPT DHPMIMRANE EHLSWEAFKV VLEQLLAAVE KDDYSRVRQL
651  LRETVSGYAP DGEIVDWIYR QRRREP
```

FIGURE 13

```
   1 atgcaccacc accaccacca cggttccatg ttcgtctgg ccatgcgcca
  51 gtattcatg ggagactggt actctgctgt gcagtcggta ccatttctca
 101 accgccagga tggctgccc agggtggcta tctatggcgc ggggcggcc
 151 gccaaccagt tggttgcggc attgcgtctc ggtcgggcga tgcgtccggt
 201 ggcgttcatc gatgatgaca agcagatcgc caaccgggtc atcgccggtc
 251 tgcgggtcta taccgccaag catatccgcc agatgatcga cgagacgggc
 301 gcgcaggagg ttctcctggc gattccttcc gccactcggg cccggcgccg
 351 agagattctc gagtccctgg agccgttccc gctgcacgtg cgcagcatgc
 401 ccggcttcat ggacctgacc agcggccggg tcaaggtgga cgacctgcag
 451 gagtggaca tcgctgacct gctggggcgc gacagcgtcg caccgcgcaa
 501 ggagctgctg gaacgttgca tccgcggtca ggtggtgatg gtgaccgggg
 551 cgggcggctc tatcggttcg gaactctgtc ggcagatcat gagttgttcg
 601 cctagcgtgc tgatcctgtt cgagcacagc gaatacaacc tctatagcat
 651 ccatcaggaa ctggagcgtc ggatcaagcg cgagtcgctt tcggtgaacc
 701 tgttgccgat cctcggttcg gtgcgcaatc ccgagcgcct ggtggacgtg
 751 atgcgtacct ggaaggtcaa taccgtctac catgcggcgg cctacaagca
 801 tgtgccgatc gtcgagcaca acatcgccga gggcgttctc aacaacgtga
 851 taggcacctt gcatgcggtg caggccgcgg tgcaggtcgg cgtgcagaac
 901 ttcgtgctga tttccaccga caaggcggtg cgaccgacca atgtgatggg
 951 cagcaccaag cgcctggcgg agatggtcct tcaggcgctc agcaacgaat
1001 cggcaccgtt gctgttcggc gatcggaagg acgtgcatca cgtcaacaag
1051 acccgtttca caatggtccg cttcggcaac gtcctcggtt cgtccggttc
1101 ggtcattccg ctgttccgcg agcagatcaa gcgcggcggc ccggtgacgg
1151 tcacccaccc gagcatcacc cgttacttca tgaccattcc cgaggcagcg
1201 cagttggtca tccaggccgg ttcgatgggg cagggcggag atgtattcgt
1251 gctggacatg gggccgccgg tgaagatcct ggagctgccc gagaagatga
1301 tccacctgtc cggcctgagc gtgcgttccg agcgttcgcc ccatggtgac
1351 atcgccatcg agttcagtgg cctgcgtcct ggcgagaagc tctacgaaga
1401 gctgctgatc ggtgacaacg tgaatcccac cgaccatccg atgatcatgc
1451 gggccaacga ggaacacctg agctgggagg ccttcaaggt cgtgctggag
1501 cagttgctgg ccgccgtgga gaaggacgac tactcgcggg ttcgccagtt
1551 gctgcgggaa accgtcagcg gctatgcgcc tgacggtgaa atcgtcgact
1601 ggatctatcg ccagaggcgg cgagaaccct ga
```

FIGURE 14

```
...1 MHHHHHHGSM LRLAMRQYFM GDWYSAVQSV PFLNRQDGLP RVAIYGAGAA
..51 ANQLVAALRL GRAMRPVAFI DDDKQIANRV IAGLRVYTAK HIRQMIDETG
.101 AQEVLLAIPS ATRARRREIL ESLEPFPLHV RSMPGEMDLT SGRVKVDDIQ
.151 EVDIADLLGR DSVAPRKELL FRCIRGQVVM VTGAGGSIGS ELCRQIMSCS
.201 PSVLILFEHS EYNLYSIHQE LERRIKRFSL SVNLLPIIGS VRNPERLVDV
.251 MRTWKVNTVY HAAAYKHVPI VEHNIAEGVL NNVIGTLHAV QAAVQVGVQN
.301 FVLISTDKAV RPTNVMGSTK RLAFMVLQAL SNFSAPLLFG DRKDVHHVNK
.351 TRFTMVRFGN VLGSSGSVIP LFREQIKRGG PVTVTHPSIT RYFMTIPEAA
.401 QLVIQAGSMC QGGDVFVLDM GPPVKILELA EKMIHLSGLS VRSERSPHGD
.451 IAIFFSGLRP GEKLYEELLI GDNVNPTDHP MIMRANEEHL SWEAFKVVLE
.501 QLLAAVEKDD YSRVRQLLRE TVSCYAPDGE IVDWIYRQRR RFP
```

FIGURE 15

```
   1 atgcaccacc accaccacca cggttccatg ttggataact tgcgtggacg
  51 cctcctggga ttgccgcgcc gccagaagcg cattcttcag gttgcgacgg
 101 acatcggcct ggtgtggctt tcattgtggc tggctttcct ggtgcgtctc
 151 ggcaccgaag acatgatcga tccgttcggg gatcacgcct ggctgttcat
 201 agcggcgcct ctaaccgcca tcccgctctt catccgcttc ggcatgtacc
 251 gggcggtgat gcgctacctg ggcaacgacg ccctatcgc gatcgccaag
 301 gccgtcacca tttccgcgct ggtcctgtcg ttgctggtct actggtaccg
 351 ctccccgccg gcggtggtgc cccgttccct ggtgttcaac tactggtggt
 401 tgagcatgct gctgatcggc ggcttgcgtc tggccatgcg ccagtatttc
 451 atgggcgact ggtactctgc tgtgcagtcg gtaccatttc tcaatcgcca
 501 ggatggcctg cccagggtgg ccatctatgg cgcggggcg gccggcaacc
 551 agttggttgc ggcattgcgt ctcggtcggg cgatgcgtcc ggtggcgttc
 601 atcgatgacg acaagcagat cgccaaccgg gtcatcgccg gtctgcgggt
 651 ctataccgcc aagcatatcc gccagatgat cgacgagacg ggcgcgcagg
 701 aggttctcct ggcgattcct tccgccactc gggccggcg ccgagagatt
 751 ctcgagtccc tggagccgtt cccgctgcac gtgcgcagca tgcctgggtt
 801 catggacctg gccagcggtc gggtcaaggt ggacgaccig caggaggtgg
 851 acatcgctga cctgctgggg cgcgacagcg tcgcaccgcg caaggagctg
 901 ctggaacggt gcatccgcgg tcaggtggtg atggtgaccg gagcgggcgg
 951 ttctatcggt tcggaactct gtcggcagat catgagttgt tgcctagcg
1001 tgctgatcct gttcgagcac agcgaataca acctctacag catccatcag
1051 gaactggagc gtcggatcaa gcgcgagtcg cttccggtga acctgttgcc
1101 gatcctcggt tcggtgcgca atcccgagcg cctggtggac gtgatgcgta
1151 cctggaaggt caataccgtc taccatgcgg cggcctacaa gcatgtgccg
1201 atcgtcgagc acaacatcgc cgaggcgttc ctcaacaacg tgataggcac
1251 cttgcatgcg gtgcaggccg cggtgcaggt cggcgtgcag aacttcgtgc
1301 tgatttccac cgacaaggcg gtgcggccga ccaatgtgat gggcagcacc
1351 aagcgcctgg cggagatggt ccttcaggcg ctcagcaacg aatcggcacc
1401 ggtgctgttc ggcgatcgga aggacgtgca tcacgtcaac aagacccgtt
1451 tcaccatggt ccgcttcggc aacgtcctcg gttcgtccgg ttcggtcatt
1501 ccgctgttcc gcgagcagat caagcgcggc ggcccggtga cggtcaccca
1551 cccgagcatc acccgttact tcatgaccat tcccgaggcg gcgcagttgg
1601 tcatccaggc cggttcgatg gggcaggcg gagatgtatt cgtgctggac
1651 atgggccgc cggtgaacat cctggagctc gccgagaaga tgatccacct
1701 gtccggcctg agcgtgcgtt ccgagcgttc gccccatggt gacatcgcca
1751 tcgagttcag tggcctgcgt cctggcgaga agctctacga agagctgctg
1801 atcggtgaca acgtgaatcc caccgaccat ccgatgatca tgcgggccaa
1851 cgaggaacac ctgagctggg aggccttcaa ggtcgtgctg gagcagttgc
1901 tggccgccgt ggagaaggac gactactcgc gggttcgcca gttgctgcgg
1951 gaaatcgtca gcggctatgc gcctgacggt gaaatcgtcg actggatcta
2001 tcgccagagc cggcgagaac cctga
```

FIGURE 16

```
  1 MHHHHHHGSM LDNLRGRLLG LPRRQKRILQ VATDIGLVWL SLWLAFLVRL
 51 GTEDMIDPFG DHAWLFIAAP LTAIPLFIRF GMYRAVMRYL GNDALIAIAK
101 AVTISALVLS LLVYWYRSPP AVVPRSLVFN YWWLSMLLIG GLRLAMRQYF
151 MGDWYSAVQS VPFLNRQDGL PRVAIYGAGA AGNQLVAALR LGRAMRPVAF
201 IDDDKQIAKR VIAGLRVYTA KHIRQMIDET GAQFVLLAIP SATRARRREI
251 LESLEPFPLH VRSMPGFMDL ASGRVKVDDL QEVDIADLLG RDSVAPRKEL
301 LERCIRGQVV MVTGAGGSIG SFLCRQIMSC SPSVLILFEH SFYNLYSTHQ
351 ELERRIKRES LSVNLLPILG SVRNPERLVD VMRTWKVNTV YHAAAYKHVP
401 IVEHNIAEGV LNNVIGTLHA VQAAVQVGVQ NFVLISTDKA VRPTNVMCST
451 KRLAEMVLQA LSNESAPVLF GDRKDVHHVN KTRFTMVRFG NVLGSSGSVI
501 PLFRFQIKRG GPVTVTHPSI TRYFMTIPEA AQLVIQAGSM GQGGDVFVLD
551 MGPPVNILEL AFKMIHLSGL SVRSERSPHG DIAIEFSGLR PGEKLYEELL
601 IGDNVNPTDH PMIMRANFFH LSWEAFKVVL EQLLAAVEKD DYSRVRQLLR
651 FIVSGYAPDG EIVDWIYRQR RREP
```

METHOD FOR ASSAYING THE FUNCTION OF FLAA1 AND WBPM

This application claims benefit from U.S. provisional application serial No. 60/136,564 on May 28, 1999.

FIELD OF THE INVENTION

The invention relates to methods for measuring the activity of FlaA1, WbpM and homologues thereof and methods for the isolation and of inhibitors of FlaA1 and WbpM and homologues thereof which are useful as antimicrobial agents.

BACKGROUND OF THE INVENTION

The opportunistic pathogen *P. aeruginosa* remains a problem in the nosocomial infection of immunocompromised individuals. *P. aeruginosa* infections are particularly a problem in burn patients, people receiving medical implants, and in individual suffering from cystic fibrosis (Fick, R. B. Jr., 1993). The organism is intrinsically resistant to many antibiotics and capable of forming biofilms which are recalcitrant to treatment. Several virulence factors have been identified in the pathogenesis of *P. aeruginosa* infections, including proteins such as exotoxin A, proteases, and exopolysaccharides including alginate and lipopolysaccharide (LPS). The LPS of *P. aeruginosa* is typical of Gram-negative bacteria, composed of lipid A-core oligosaccharide-O antigen repeating units.

*P. aeruginosa* is capable of coexpressing two distinct forms of LPS, designated A-band and B-band LPS, respectively. A-band LPS is a shorter, common form expressed by the majority of *P. aeruginosa* serotypes, and has a trisaccharide repeating unit of α-D-rhamnose linked 1→3, 1→3, 1→2. B-band LPS is the serotype-specific, O-antigen-containing form, and is a heteropolymer composed of di- to pentasaccharide repeats containing a wide variety of acyl sugars, amino sugars, and uronic acids. Both the A- and B-band repeating units are attached to lipid A-core, but there appears to be differences between them regarding point of attachment to and composition of the outer core region (Rivera et al., 1992).

The gene clusters for biosynthesis of core oligosaccharides/O-antigens rfb have been cloned and characterized from several bacterial species, including some from non-enteric genera such as Bordetella (Allen and Maskell, 1996), Haemophilus (Jarosik and Hansen, 1994), Neisseria (Gotschlich, 1994), Vibrio (Stroeher et al., 1992; Amor and Mutharia, 1995; Comstock et al., 1996), and Xanthamonas (Kingsley et al., 1993).

The clusters of genes involved in the biosynthesis of the O-antigen for serotype O5 and O6 of *Pseudomonas aeruginosa* have recently been sequenced (Burrows et al. 1996; Belanger et al. 1999). Based on sequence homologies, putative enzymatic functions have been assigned to the various gene products, and pathways have been proposed for the synthesis of specific sugar derivatives that constitute the O-antigen tri-saccharide repeats. WbpM is an essential gene required for expression of B-band LPS in both serotypes. The WbpM gene is conserved among all 20 serotypes of *P. aeruginosa,* and homologues have also been identified in a large number of bacterial pathogens including *Helicobacter pylori* (Allen and Maskell (1996); Lin W. S. et al. (1994); Comstock L. E. et al. (1996); Zhang, L. et al. (1997); Tomb, J.-F. et al. (1997)).

WbpM is a large protein of 665 amino acids (75 kDa). The C-terminus portion of the protein presents 4 domains that are conserved among all WbpM homologues. The precise function of the encoded protein WbpM is not known, but knock-out experiments have shown that it is essential for B-band LPS biosynthesis in several serotypes, including serotype O5. Sequence analysis suggests that it might be involved in the biosynthesis of UDP-N-acetylfucosamine. Prior to the present invention it was unknown whether WbpM was a $C_4$ epimerase catalyzing the conversion of UDP-N-acetylglucosamine to UDP-N-acetylgalactosamine, or if it was a dehydratase involved in the conversion of UDP-N-acetylgalactosamine to UDP-N-acetylfucosamine.

*Helicobacter pylori* (*H. plori*) is a microaerophilic Gram-negative bacteria that has been associated with gastric diseases such as ulcers and cancers (Warren and Marshall 1983, Graham 1991, Peterson 1991). It is present chronically in 70–90% of the population in developing countries (Dunn et al. 1997) but its mode of transmission and its potential initial reservoir are not known. This organism is well adapted to the hostile environment in which it thrives, thanks to the production of high level of urease to neutralize acidic pH (Smoot et al. 1990). Its virulence has been associated with its motility that is conferred by a unipolar sheated flagella (Josenhans et al. 1995, Eaton et al. 1992), with its capacity to create acidic vacuoles in epithelial cells (Labigne and De Reuse 1996), as well as with its lipopolysaccharide (LPS) (Muotiala et al. 1992). The LPS of *H. pylori* exhibits structural features also found at the surface of human blood cells such as the presence of Lewis X and Y antigenic determinants (Aspinall and Monteiro 1996; Aspinall et al. 1996). Such structures are thought to play a role as molecular mimics that allow the organism to evade host immunity defences (Sherburne and Taylor 1995).

The entire genomes of *H. pylori* strains 26695 and J99 have been sequenced recently (Tomb et al. 1997; Alm et al. 1999). Though the genomes are quite small compared with that of other Gram-negative bacteria, numerous open reading frames (ORF) could not be assigned a putative function based on sequence homologies. This is mainly due to the fact that, contrarily to other well studied gram-negative bacteria, the genome of *H. pylori* is not organised into operons which regroup genes involved in the same biological functions into defined clusters. In cases where only low sequence homologies with genes from other organisms are observed, the gene position is not useful to assign a putative function. FlaA1 (HP0840) is one of these ORFs found in strain 26695. It was originally assigned a flagellar-related function, hence its name, though it is not linked to any other flagellar biosynthetic and/or assembly genes. The original assignment is consistent with the existence of two homologues of FlaA1 found in *Caulobacter crescentus* (FlmA, Leclerc et al. 1998) and in *Campylobacter jejuni* (PglF, Szymanski et al. 1999). Both have been shown to be involved in glycosylation of flagella proteins by knock-out analysis. However, no biochemical evidence is available to assign a specific enzymatic function to the gene products. Moreover, glycosylation of flagella has not been demonstrated in *H. pylori* itself, although it has been demonstrated in several species of Campylobacter (Doig et al. 1996, Szymanski et al. 1999), which is closely related to *H. pylori*.

As the FlaA1 or WbpM enzymes are not present in higher organisms (such as mammals) they represent good drug target candidates for the development of new antimicrobial agents that would be efficient against *H. pylori* or *P. aeruginosa* as well as other organisms that produce homologues of FlaA1 or WbpM. However, before new antimicrobial agents can be developed, the biochemical pathways that are catalysed by the enzymes must be determined.

SUMMARY OF THE INVENTION

The present inventors have determined that a series of homologous enzymes from a variety of human bacterial pathogens are $C_6$ sugar-nucleotide dehydratases. In particular, the inventors have shown that FlaA1 from *Helicobacter pylori*, WbpM from *Pseudomonas aeruginosa*, BplL from *Bordetella pertussis*, Cap8D from *Staphylococcus aureus* and TrsG from *Yersinia enterocolitica* are $C_6$-dehydratases which allows the development of biochemical assays to detect these enzymes as well as the isolation of agents that inhibit these enzymes. Agents that inhibit the enzymes can be used to combat the bacterial pathogens containing the enzymes.

In one aspect, the present invention provides an assay for measuring the activity of or detecting FlaA1, WbpM and functional homologues thereof. In particular, the present invention provides a spectrophotometric assay for measurement of the activity of FlaA1, WbpM or a homologue thereof that is substrate/product specific.

Accordingly, the present invention provides a method for detecting an enzyme with FlaA1-like activity in a sample comprising the steps of: (a) incubating the sample with UDP-GlcNAc; (b) stopping the reaction; and (c) determining if there has been a decrease in UDP-GlcNAc in the sample, wherein a decrease in UDP-GlcNAc indicates the presence of an enzyme with FlaA1-like activity.

In another aspect, the present invention provides an assay for detecting inhibitors of FlaA1, WbpM or a homologue thereof. Accordingly, the present invention further provides a method for screening for an inhibitor of an enzyme with FlaA1-like activity comprising (a) incubating a test sample containing (i) an enzyme with FlaA1-like activity, (ii) a substance suspected of being an inhibitor of the enzyme; and (iii) UDP-GlcNAc; (b) stopping the reaction; (c) comparing the amount of UDP-GlcNAc in the test sample with the amount in a control sample (that does not contain the substance suspected of being an inhibitor) wherein a decrease in the amount of GlcNAc in the control sample as compared to the test sample indicates that the substance is an inhibitor of the enzyme.

In a further aspect, the present invention provides a method for preparing UDP-N-acetyl quinovosamine (UDP-QuiNAc) using the FlaA1 enzyme or a homologue thereof and UDP-GlcNAc as a substrate.

BRIEF DESCRIPTION OF THE FIGURES

FIG. 2 and SEQ.ID.NO.:1 shows the DNA sequence of FlaA1 from *Helicobacter pylori* carrying a N-terminal hexahistidine tag (in bold).

FIG. 3 and SEQ.ID.NO.:2 shows the amino acid sequence of FlaA1 from *Helicobacter pylori* carrying a N-terminal hexahistidine tag (bold).

FIG. 11 and SEQ.ID.NO.:3 shows the DNA sequence of WbpM05 carrying a N-terminal hexahistidine tag (in bold).

FIG. 12 and SEQ.ID.NO.:4 shows the amino acid sequence of WbpM05 carrying a N-terminal hexahistidine tag (in bold).

FIG. 13 and SEQ.ID.NO.:5 shows the DNA sequence of WbpMΔ1-132 carrying a N-terminal hexahistidine tag (in bold).

FIG. 14 and SEQ.ID.NO.:6 shows is the amino acid sequence of WbpMΔ1-132 from *Pseudomonas aeruginosa* carrying a N-terminal hexahistidine tag (in bold).

FIG. 15 and SEQ.ID.NO.:7 shows the DNA sequence of WbpM06 carrying a N-terminal hexahistidine tag (in bold).

FIG. 16 and SEQ.ID.NO.:8 shows the amino acid sequence of WbpM06 from *Pseudomonas aeruginosa* carrying a N-terminal hexahistidine tag (in bold).

DETAILED DESCRIPTION OF THE INVENTION

Figure 1:
FIG. 1 is a schematic diagram showing the domain analysis of FlaA1, WbpM and their homologues.

Prior to the present invention, it was unknown whether WbpM and its homologues had dehydratase or epimerase activity. A Gapped BLASTP search of the GenBank database (Altschul et al., 1997) revealed a large number of WbpM homologues in both Gram-negative and Gram-positive bacteria, as well as the Archae (Table 2). These homologues could be divided into two subfamilies. Subfamily 1, including WbpM, contains large (approximately 600 amino acids) proteins with two distinct domains, with an NAD+/NADP+ binding motif in the C-terminus, and often a second motif in the N-terminus (Burrows et al., 1996). The other sub-family, embodied by open reading frame (ORF) HP0840 (FlaA1; Tomb et al., 1997), consists of smaller (between 300 and 400 amino acids) proteins that are homologous to the C-terminal half of the larger proteins in the other subfamily (Burrows et al., 1996, Table 1). Interestingly, some species of bacteria contain examples of both subfamilies. In the capsular biosynthetic clusters of *Staphylococcus aureus* serotypes 5 and 8, contiguous large (capD) and small (capE) wbpM homologues are present in the same operon (Sau and Lee, 1996, Sau et al., 1997), whereas *S. aureus* M serotype 1 has only capD (Lin et al., 1994).

Although the specific function of these proteins had not yet been demonstrated at the biochemical level, they were shown by complementation to be functionally homologous. The wbpM homologues from *B. pertussis*, *S. aureus* serotype 8, and *H. pylori* were individually cloned into the broad host range vector, pUCP26 (West et al., 1994) (Table 2) and used to transform a *P. aeruginosa* O5 wbpM::Gm mutant, which cannot synthesize B-band LPS (Burrows et al., 1996). Silver-stained SDS-PAGE and Western immunoblot analyses showed that the *P. aeruginosa* wbpM::Gm mutant was complemented for O-antigen production by wlbL (Allen and Maskell, 1996), cap8D (Sau and Lee, 1996) and by FlaA1 (see Example 1). The ability of FlaA1 to complement a wbpM mutation demonstrates that the subfamily 2 homologues have the same activity as the subfamily 1 forms.

The inventors used a refined sequence analysis using the MEME motif discovery software (www.sdsc.edu.MEME)

and revealed the existence of 4 very conserved domains that are present in the same order and same spacing within the sequences of these homologues as shown in FIG. 1. The conserved domains are shown as boxes. The entire data base was searched using these 4 conserved domain sequences with the MAST (Motif Alignment and Search Tool) program. It led to the discovery of FlaA1 and numerous additional homologues of unknown function that display the same conserved domains in the same pattern. Most homologues are large membrane proteins like WbpM. However, FlaA1 only corresponds to the soluble terminal half of WbpM. Hence it represents an ideal candidate to determine the biochemical function of this entire family of enzymes. The inventors have shown that FlaA1 can fully complement a WbpM knock-out which demonstrates that WbpM and FlaA1 are functionally equivalent. This demonstrates that FlaA1 is useful as a screening tool not only to develop inhibitors against FlaA1 but also against WbpM and other functional homologues.

(a) Detection of Enzymes with FlaA1-like Activity

The inventors have developed a spectrophotometric assay in order to detect the presence of FlaA1, WbpM or a homologue thereof. The assay relies on the differential colorimetric yields of reaction between N-acetyl hexosamines and p-dimethylaminobenzaldehyde (DMAB). This reagent has been described previously by Reissig, Strominger and Leloir 1995 J. Biol. Chem. 217, 959–966. This assay allows the quantitation of UDP-GlcNAc or UDP-GalNAc after enzymatic reaction. Advantageously, only 10 to 20 nmol of substrate are necessary per assay, and so that the spectrophotometric detection may be advantageously carried out in microtitration plates.

Using the DMAB assay, the inventors determined that (1) FlaA1 uses UDP-GlcNAc as a substrate and (2) FlaA1 is not a $C_4$ epimerase. (See Example 1). The inventors further identified the reaction products formed by the FlaA1 enzyme using capillary electrophoresis coupled to mass spectrometry (CE and MS). In particular, using CE and MS the inventors demonstrated that FlaA1 converts UDP-GlcNAc into a 4-Keto-6 methyl-UDP-GlcNAc intermediate which is then stereospecifically reduced to UDP-QuiNAc. These results demonstrate that FlaA1 is a $C_6$-dehydratase/$C_4$ reductase.

In one aspect, the present invention provides a method for detecting an enzyme with FlaA1-like activity in a sample comprising the steps of: (a) incubating the sample with UDP-GlcNAc; (b) stopping the reaction; and (c) determining if there has been a decrease in UDP-GlcNAc in the sample, wherein a decrease in UDP-GlcNAc indicates the presence of an enzyme with FlaA1-like activity.

The term "enzyme with FlaA1-like activity" means that the enzyme is a $C_6$-dehydratase that uses UDP-GlcNAc as a substrate and includes, but is not limited to, FlaA1, WbpM, BplL, Cap8D, TrsG and functional homologues thereof. The term "functional homologue" means that the protein has the same enzymatic activity (i.e. a $C_6$-dehydratase) but not necessarily the same structure or sequence as FlaA1.

In one embodiment, the determination of whether the amount of GlcNAc has decreased is done by quantitating the amount of UDP-GlcNAc in the sample. Accordingly, the present provides a method for assaying an enzyme with FlaA1-like activity in a sample comprising the steps of: (a) incubating the sample with UDP-GlcNAc; (b) stopping the reaction; and (c) quantifying the amount of UDP-GlcNAc in the sample, wherein a decrease in UDP-GlcNAc indicates the presence of an enzyme with FlaA1-like activity. Preferably, the quantification of UDP-GlcNAc in the sample is done by spectrophotometric determination of reaction product between UDP-GlcNAc and the reagent DMAB.

In another embodiment, the determination of whether the amount of GlcNAc has decreased is done by measuring the optical density of the sample as when FlaA1 is incubated with UDP-GlcNAc, a decrease in the optical density (OD) at 595 nm is observed. Accordingly, the present invention provides a method for assaying for an enzyme with FlaA1-like activity comprising the steps of (a) incubating the sample with UDP-GlcNAc; (b) stopping the reaction; and (c) measuring the optical density of the sample wherein a decrease in optical density indicates the presence of an enzyme with FlaA1-like activity. Preferably, the optical density is measured at 595 nm. For practical reasons, the DMAB assay is carried out using a wavelength setting of 595 nm in the spectrophotometer. However, the signal of the assay could be increased by approximately 15% if the wavelength is adjusted to 580 nm.

In a preferred embodiment, samples that indicate a reduction in UDP-GlcNAc based on the above assays are further analysed by CE/MS in order to identify the reaction products of the enzyme catalysis and confirm that the enzyme is a $C_6$ dehydratase. In particular, detecting the presence of UDP-QuiNAc or 4-keto,6-methyl-GlcNAc in the sample (for example by CE/MS) after reaction with UDP-GlcNAc confirms that the enzyme is a $C_6$-dehydratase (i.e. has FlaA1-like activity).

The inventors have also shown that while the substrate UDP-GalNAc is not modified by FlaA1, the substrate does likely bind to FlaA1 as indicated by its disappearance from the solution when incubated with FlaA1. Accordingly, in a further aspect, the present invention provides a method for detecting an enzyme with FlaA1-like activity comprising the steps of (a) incubating the sample with UDP-GalNAc; (b) stopping the reaction; and (c) determining if there is a decrease in UDP-GalNAc in the sample wherein a decrease UDP-GalNAc indicates the presence of an enzyme with FlaA1-like activity. The determination of whether the amount of UDP-GalNAc in the sample has decreased can be done by (1) quantitating the amount of UDP-GalNAc in the sample, for example by spectrophotometric determination of the reaction product between UDP-GalNAc and DMAB (as described above for UDP-GlcNAc) or (2) measuring the optical density of the sample wherein a decrease in optical density indicates that the amount of UDP-GalNAc has decreased. Further, a decrease in the optical density obtained when using UDP-GalNAc as a substrate excludes the possibility that the enzyme being tested has epimerase activity.

While the above assays for detecting an enzyme with FlaA1-like activity preferably measure UDP-GlcNAc or UDP-GalNAc (most preferably UDP-GlcNAc), one skilled in the art will appreciate that other methods may be used to determine if the test sample contains an enzyme with FlaA1-like activity. For example, the sample may be assayed for the reaction products of the catalysis of UDP-GlcNAc by a FlaA1-like enzyme such as UDP-QuiNAc or 4-keto,6-methyl-GlcNAc. Accordingly the present invention provides a method for detecting an enzyme with FlaA1-like activity comprising the steps of (a) incubating the sample with UDP-GlcNAc; (b) stopping the reaction; and (c) detecting the presence of UDP-QuiNAc and/or 4-keto,6-methyl-GlcNAc in the sample, wherein the presence of UDP-QuiNAc and/or 4-keto,6-methyl-GlcNAc indicates the presence of an enzyme with FlaA1-like activity. The presence of UDP-QuiNAc and/or 4-keto,6-methyl-GlcNAc may be determined by CE/MS as described herein.

(b) Detection and Use of Inhibitors of FlaA1-like Activity

The present invention also includes an assay to screen for inhibitors of an enzyme with FlaA1-like activity. Accordingly, the present invention includes a method for screening for an inhibitor of an enzyme with FlaA1-like activity comprising (a) incubating a test sample containing (i) an enzyme with FlaA1-like activity, (ii) a substance suspected of being an inhibitor of the enzyme; and (iii) UDP-GlcNAc; (b) stopping the reaction; (c) comparing the amount of UDP-GlcNAc in the test sample with the amount in a control sample (that does not contain the substance suspected of being an inhibitor) wherein a decrease in the amount of GlcNAc in the control sample as compared to the test sample indicates that the substance is an inhibitor of the enzyme.

In one embodiment, the amount of UDP-GlcNAc in the test and control samples is compared by quantifying the amount of UDP-GlcNAc using the DMAB assay as described above.

In an alternate embodiment, the present invention provides a method for screening for an inhibitor of an enzyme with FlaA1-like activity comprising (a) incubating a test sample containing (i) an enzyme with FlaA1-like activity, (ii) a substance suspected of being an inhibitor of the enzyme; and (iii) UDP-GlcNAc; (b) stopping the reaction; and (c) comparing the optical density of the test sample with the optical density of a control sample, wherein a decrease in the optical density in the control sample as compared to the test sample indicates that the substance is an inhibitor of the enzyme. Preferably the optical density is measured at 595 nm.

The above described screening assays may also be carried out using UDP-GalNAc as a substrate as described under (a) above. Further, the assays may also be carried out by detecting one of the reaction products of UDP-GlcNAc catalysis (such as UDP-QuiNAc or 4-keto,6-methyl-GlcNAc) wherein the presence of a reaction product indicates that the substance is not an inhibitor.

Preferably, the enzyme used in the screening assays is FlaA1 which is advantageous because it can be overproduced in high yields using the expression systems developed by the inventors.

Inhibitors of an enzyme with FlaA1-like activity may be useful as antimicrobial agents against organisms that produce an enzyme with FlaA1-like activity. In one embodiment, the assay is used to isolate inhibitors of FlaA1 and can be used to treat infections caused by *Helicobacter pylori, Pseudomonas aeruginosa, Bordetella pertussis, Staphylococcus aureus* and *Yersinia enterocolitica*. Accordingly, the present invention also provides a method of treating a microbial infection comprising administering an effective amount of an inhibitor of an enzyme with FlaA1-like activity to an animal in need thereof. Preferably, the inhibitor has been isolated according to one or more of the above described screening methods of the invention.

The term "effective amount" as used herein means an amount effective, at dosages and for periods of time necessary to achieve the desired result.

The term "animal" as used herein includes all members of the animal kingdom including humans.

The present invention also includes pharmaceutical compositions comprising an inhibitor of an enzyme with FlaA1-like activity in admixture with a pharmaceutically acceptable diluent or carrier. Preferably, the inhibitor has been isolated according to one or more of the above described screening methods of the invention.

The pharmaceutical composition may be administered in a convenient manner such as by injection (subcutaneous, intravenous, etc.), oral administration, inhalation, intranasal, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The present invention further includes kits comprising reagents suitable for applying the methods of the invention to identify inhibitors of a FlaA1-like enzyme. The kits may also include suitable instructions for performing the methods of the invention.

(c) Method of Producing UDP-QuiNAc

In a further aspect, the present invention provides a method for preparing UDP-N-acetyl quinovosamine (UDP-QuiNAc) using the FlaA1 enzyme or a homologue thereof and UDP-GlcNAc as a substrate. As mentioned previously, FlaA1 converts UDP-GlcNAc into a 4-keto-6-methyl UDP-GlcNAc intermediate which is then stereospecifically reduced to UDP-QuiNAc. Since only one enzyme (i.e., FlaA1) is needed to make the product, the yields of the product are very high and the conversion to the final product is achieved very efficiently. Importantly, UDP-QuiNAc is not currently commercially available. Accordingly, the present invention provides a method for preparing UDP-N-acetyl-quinovosamine (UDP-QuiNAc) comprising incubating FlaA1 or an enzyme with FlaA1-like activity with the substrate UDP-GlcNAc under conditions suitable for the production of UDP-Qui-NAc.

(d) Antibodies

The invention further provides the production of specific antibodies to FlaA1, WbpM and their homologues. These antibodies can be used to detect FlaA1, WbpM and their homologues in a sample. In particular, the present inventors have prepared antibodies against the Δ1-132 WbpM protein and have shown that these antibodies also react with homologues of WbpM and FlaA1.

Accordingly, the present invention provides a method for detecting FlaA1, WbpM or a homologue thereof, in a sample, comprising the steps of: (1) contacting the sample with antibodies to FlaA1, WbpM or a homologue thereof under conditions favourable for the formation of complexes between said antibodies and said FlaA1, WbpM or a homologue thereof; and (2) assaying for the presence of any complexes formed. If a complex is formed, the FlaA1, WbpM or homologue thereof can be isolated from the sample and assayed for FlaA1-like activity using the DMAB assay described above. If desired, the reaction products can be further analyzed using CE/MS.

Antibodies to FlaA1, WbpM and their homologues may also be used to inhibit the activity of FlaA1, WbpM and their homologues. The ability of such antibodies to inhibit FlaA1, WbpM and their homologues may be assayed using the DMAB assay described herein, and all such antibodies are within the scope of the present invention.

Antibodies that bind FlaA1, WbpM and their homologues can be prepared using techniques known in the art such as those described b Kohler and Milstein, Nature 256, 495 (1975) and in U.S. Pat. Nos. RE 32,011, 4,902,614, 4,543,439, and 4,411,993 which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Within the context of the present invention, antibodies are understood to include monoclonal antibodies, polyclonal antibodies, antibody fragments (e.g., Fab, and F(ab')$_2$) and recombinantly produced binding partners. Antibodies are understood to be reactive against the FlaA1, WbpM and their homologues if they bind to the protein with an affinity of greater than or equal to $10^{-6}$ M. As will be appreciated by one of ordinary skill in the art, antibodies may be developed which not only bind to the protein, but which bind to a regulator of the protein, and which also block the biological activity of the protein.

Polyclonal antibodies may be readily generated by one of ordinary skill in the art from a variety of warm-blooded animals such as horses, cows, various fowl, rabbits, mice, or rats. Briefly, FlaA1, WbpM or a homologue, or portions thereof, may be used to immunize an animal. An animal may be immunized through intraperitoneal, intramuscular, intraocular, or subcutaneous injections, in conjunction with an adjuvant such as Freund's complete or incomplete adjuvant. Following several booster immunizations, samples of serum are collected and tested for reactivity to the protein. Particularly preferred polyclonal antisera will give a signal on one of these assays that is at least three times greater than background. Once the titer of the animal has reached a plateau in terms of its reactivity to the receptor protein, larger quantities of antisera may be readily obtained either by weekly bleedings, or by exsanguinating the animal.

Monoclonal antibodies may also be readily generated using conventional techniques as described herein. Generally, hybridoma cell lines are prepared by a process involving the fusion under appropriate conditions of an immortalizing cell line and spleen cells from an animal appropriately immunized to produce the desired antibody. Immortalizing cell lines may be murine in origin however, cell lines of other mammalian species may be employed including those of rat, bovine, canine, human origin, and the like. The immortalizing cell lines are most often of tumor origin, particularly myeloma cells but may also include normal cells transformed with, for example, Epstein Barr Virus. Any immortalizing cell may be used to prepare the hybridomas of the present invention.

Antibody producing cells may be employed as fusion partners such as spleen cells or peripheral blood lymphocytes. The animal from which the cells are to be derived may be immunized at intervals with peptides derived from FlaA1,WbpM or their homologues.

The immortalizing cells and lymphoid cells may be fused to form hybridomas according to standard and well-known techniques employing polyethylene glycol as a fusing agent. Alternatively, fusion may be accomplished by electrofusion.

Hybridomas are screened for appropriate monoclonal antibody secretion by assaying the supernatant or protein purified from the ascites for reactivity. The hybridomas are screened for antibodies which have the desired properties e.g. inhibit the dehydratase activity of FlaA1, WbpM or their homologues (depending upon which was used to generate the monoclonal).

The term "antibody" as used herein is intended to include fragments thereof which also specifically react with FlaA1, WbpM protein or their homologues, or peptide thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of WbpM or homologue antigens of the invention (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with FlaA1, WbpM protein or their homologues as described herein can be further humanized by producing human constant region chimeras, in which parts of the variable regions, particularly the conserved framework regions of the antigen-binding domain, are of human origin and only the hyper-variable regions are of non-human origin. Such immunoglobulin molecules may be made by techniques known in the art, (e.g., Teng et al., Proc. Natl. Acad. Sci. U.S.A., 80, 7308–7312 (1983); Kozbor et al., Immunology Today, 4, 7279 (1983); Olsson et al., Meth. Enzymol., 92, 3–16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against FlaA1, WbpM or their homologues may also be generated by screening expression libraries encoding immunoglobulin genes, or portions thereof, expressed in bacteria with peptides of FlaA1, WbpM or their homologues. For example, complete Fab fragments, VH regions and FV regions can be expressed in bacteria using phage expression libraries (See for example Ward et al., Nature 341, 544–546; (1989); Huse et al., Science 246, 1275–1281 (1989); and McCafferty et al. Nature 348, 552–554 (1990)). Alternatively, a SCID-hu mouse, for example the model developed by Genpharm, can be used to produce antibodies, or fragments thereof.

The following non-limiting examples are illustrative of the present invention.

EXAMPLES

Example 1

Functional Characterization of FlaA1

Materials and Methods

Materials—Unless stated otherwise, all chemical reagents used were from Sigma (St. Louis, Mo.). Restriction enzymes and T4 DNA ligase were from Gibco/BRL (Gaitherburg, Md.). Pwo DNA polymerase was from Boehringer- Mannheim (Laval, Quebec). The dNTPs were from Perkin Elmer (Markham, ON). The pentaHis anti-histidine tag antibody was from Qiagen (Santa Clarita, Calif.). Agar was from Difco (Detroit, Mich.). All kits or enzymes were used following the manufacturer's instructions.

Cloning and overexpression of FlaA1 in the pCT system

The gene encoding FlaA1 (HP0840) was obtained from the TIGR/ATCC microbial genome special collection (construct GHPEP02). The gene flaA1 was subcloned in the AflIII and BamHI sites of a pET23 derivative (Newton and Mangroo, 1999) with a N-terminal histidine tag. The sequence of the primers used to amplify flaA1 by PCR from the GHPEP02 plasmid were

5'ACTGTACATGTCAATGCCAAATCATCAA
        AAC3'     (SEQ.ID.NO.:9)

and

5'AAGCTGGATCCTCATAATAATTTCAAC
        AA3'     (SEQ.ID.NO.:10)

for the top and bottom primers, respectively. The PCR reaction consisted 100 ng of DNA, 0.5 $\mu$M each primer, 0.2 mM each dNTP, 4 mM MgCl2 and 1× buffer in a total of 50 $\mu$l. A 5 min denaturation at 94° C. was done before addition of DNA polymerase (1.5 units of Expand Long Range Template). This was followed by 20 cycles of 1 min at 94° C., 30 sec. at 40° C. and 90 sec at 68° C. A final 7 min elongation was performed at 68° C. The constructs obtained were checked by restriction analysis and sequencing. FIGS. 2 and 3 provide the DNA sequence and protein sequence, respectively, of FlaA1 carrying the N-terminal hexahistidine tag.

The construct was subsequently transformed into the expression strain BL21(DE3)pLysS (Novagen, Madison, Wis.) with ampicillin (100 $\mu$g/ml) and chloramphenicol (35 $\mu$g/ml) selection. For protein expression, 2 ml of an overnight culture were inoculated into 100 ml of TB in the presence of ampicillin and chloramphenicol. The culture was grown at 37° C. When the OD600 nm reached 0.6, IPTG (Promega, Madison, Wis.) was added to a final concentration of 1 mM and expression was allowed to proceed for no more than 5 h at 37° C. Cells were harvested by centrifugation at 5,000 g for 15 min at 4° C. and the pellet was stored at −20° C. until needed. Expression was monitored by SDS-PAGE analysis, with Coomassie blue staining or Western immunoblot using the pentaHis anti-histidine tag antibody as instructed by the manufacturer.

Subcloning of the histidine tagged FlaA1 from pLT23 to pUCP26

The FlaA1 gene with its histidine tag and with the vector ribosome binding site was subcloned from the pET construct into the complementation vector pUCP26 (West et al. 1994) by PCR. The primers used were 5'TAATACGACTCAC-TATAG3' (SEQ.ID.NO.:11) and 5'CAACTGCAGTCAT-AATAATTTCAACAA3' (SEQ.ID.NO.:12) for the top and bottom primers, respectively. The top primer is specific for the pET vector and primes upstream of a Xba I site and upstream of the ribosome binding site. The bottom primer is specific for FlaA1 and includes a PstI site. The PCR reaction was set up as described above but the higher proof reading polymerase Pwo was used instead of Expand and the elongation was carried out at 68° C. The PCR product was digested with XbaI and PstI and cloned into pUCP26 that had been digested with the same enzymes. Cloning was performed in *E. coli* DH5a under repressing conditions (0.2% glucose) to ensure recovery of correct clones. The candidate clones were sequenced over the entire length of the construct.

Complementation of a *P. aeruginosa* WbpM knock-out by His-FlaA1

The His-FlaA1/pUCP26 construct was introduced into a calcium chloride competent knock-out of WbpM in *P. aeruginosa* serotype O5 (Burrows et al. 1996). The transformation was done under repressing conditions (0.2% glucose). LPS were prepared using the Hitchcock and Brown method from overnight cultures grown in LB without repression. The LPS were analysed by SDS-PAGE followed by silver staining (FIG. 4) or Western blotting using A-band (N1F10) or B-band (Ac6TD3) LPS specific monoclonal antibodies.

Purification of over-expressed FlaA1 by chromatography

Cells sedimented from 100 ml induced culture were resuspended in 10 ml of buffer A (5 mM imidazole, 20 mM Tris pH 7, 0.1 M NaCl). The cells were briefly sonicated (macrotip, sonicator XL2020 Heat systems Incorporated, power set to 4, 2 min total, 5 sec on, 5 sec off) on ice. Cell debris were removed by centrifugation at 13 000× g for 15 min at 4° C. and the supernatant was applied to a 3 ml fast flow chelating sepharose column (Amersham-Pharmacia, Quebec) previously loaded with nickel sulfate (30 ml of 0.1 M) and equilibrated with 5 column volumes (CV) of buffer A. Loading of the sample as well as all washing and elution steps were done by gravity. After loading of the sample, the column was washed with 10 CV of buffer A and 5 CV of buffer B (20 mM imidazole, 20 mM Tris pH 7, 0.1 M NaCl). Elution was carried out with 3 CV of buffer C (1 M imidazole, 20 mM Tris pH 7, 0.5 M NaCl 0.1 M). The eluted protein was subjected to further purification by cation exchange chromatography on HS-sepharose fast flow (Pharmacia) after dilution ⅟30 in 50 mM Tris pH 7. The column (8 ml) was washed with 30 CV of Tris buffer and the protein was eluted with 3 CV of 50 mM Tris pH 7, 1 M NaCl. The eluted protein was desalted by overnight dialysis (cut off 3500 Da) in 50 mM Tris pH 7 at 4° C. The dialysed samples were concentrated by overlay with PEG 8000 (Sigma) for 4 to 5 h at 4° C. Protein quantitation was done using the BCA reagent (Pierce, Rockford, Ill.). The purified enzyme was either used fresh or stored at −20° C. in 25% gylcerol in 50 mM Tris, pH 7.

Determination of the Oligomerisation Status by Gel Filtration Analysis

A 45×1.6 cm column containing 90 ml of G100 Sephadex (Sigma, fractionation range 4–150 kDa) was used to determine the oligomerisation status of FlaA1. The column was equilibrated in 50 mM Tris pH 8 containing 100 mM NaCl and run at 1.4 ml/min. Molecular weight standards (Sigma, 12–150 kDa) were applied onto the column one by one (50–200 $\mu$g each in 200 $\mu$l). FlaA1 was applied onto the column either as a diluted solution (50 $\mu$g/200 $\mu$l deposited). Protein elution was monitored at 280 nm.

Extraction of NAD(P)+ From Purified FlaA1

A freshly purified and extensively dialysed sample of FlaA1 was concentrated up to 1.75 mg/ml of 50 mM Tris pH 7 by PEG 8000 overlay. At this concentration FlaA1 undergoes partial precipitation. The suspension (100 $\mu$l) was incubated in the presence of 10 $\mu$g of proteinase K for 45 min at 37° C. A clear solution was rapidly obtained after proteolytic digestion. It was submitted to chemical reduction by sodium borohydride (1 $\mu$l of 10 mg/ml) (Fischer, Nepean, ON) for 1 h at 37° C. The absorption spectrum was recorded before and after chemical reduction between 230 and 450 mn using a DU520 spectrophotometer (Beckman, Fullerton, Calif.) equipped with a 50 $\mu$l microcell. Serial dilutions of NAD+ (Sigma) ranging from 5 to 40 $\mu$M were prepared in 50 mM Tris pH 7 and were incubated at 37° C. for the same amount of time as FlaA1 with or without chemical reduction. The precise concentration in NAD$^1$ was calculated using $\epsilon_{260nm}$=17400 M$^{-1}$×cm$^{-1}$ and the efficiency of reduction was calculated using $\epsilon_{340nm}$=6270 M$^{-1}$×cm$^{-1}$.

Determination of the Enzymatic Conversion of UDP-GlcNAc and UDP-GalNac Using p-dimethylaminobenzaldehyde (DMAB)

Reactions were performed with a total reaction volume of 35 µl at 37° C. in 20 mM Tris pH 7 in the presence of 1.5 mM substrate and 1 mM NAD$^+$. The reactions were stopped by acid hydrolysis of the UDP moiety of the substrate. For this purpose, the samples were acidified to pH 2 by addition of 7 µl of HCl 1 N, boiled for 6 min, and neutralised by addition of 7 µl of NaOH 1 N. The spectrophotometric quantification of GalNAc and GlcNAc using DMAB was performed as described by Creuzenet et al. 2000. Briefly summarized, 100 µl of 0.2 M sodium tetraborate pH 9.1 were added to 50 µl of quenched and neutralised enzymatic reactions and boiled immediately for 3 min. 40 µl of this mixture were transferred to a microtitration plate and 200 µl of DMAB reagent (1% in glacial acetic acid/HCl 99/1 v/v) were added. After incubation for 30 min at 37° C., the OD$_{595\ nm}$ was recorded using a microplate reader. The assay was done in duplicate for each reaction tested. Standard curves were prepared using UDP-GlcNAc and UDP-GalNAc that were subjected to acid hydrolysis in the same conditions as described above.

Analysis of the Reaction Products for UDP-GlcNAc and UDP-GalNAc and Determination of the Kinetic Parameters for UDP-GlcNAc Catalysis by Capillary Electrophoresis The same reactions as above were prepared for capillary analysis using varying amounts of enzyme (440 or 54 ng) and 1 mM NAD$^+$ or not. The reaction mix was incubated for different reaction times. The specific conditions are indicated above. After incubation at 37° C. for the required amount of time, the reactions were quenched by boiling the sample for 6 min. Time course studies were performed with final sugar-nucleotide concentrations of 0.1 and 1.5 mM without NAD$^+$. Samples were quenched every 15 minutes for 2 h. For Km and V$_{max}$ determinations, the final UDP-GlcNAc concentrations ranged from 0.02 to 1.50 mM, and the reactions were quenched after 20 min of incubation with 440 ng of fresh enzyme in the absence of NAD$^+$. Reactions were also performed using varying buffers such as 20 mM sodium phosphate or bis-tris-propane at pH 7, or 20 mM sodium acetate pH 6.5 and processed for CE analysis as described above.

Capillary electrophoresis (CE) analysis were performed using a P/ACE 5000 system (Beckman, Fullerton, Calif.) with UV detection as described before (Creuzenet et al. 2000). Briefly summarised, the running buffer was 25 mM sodium tetraborate pH 9.4. The capillary was bare silica 75 µm×57 cm, with a detector at 50 cm. The capillary was conditioned before each run by washing with 0.2 M NaOH for 2 min, water for 2 min, and running buffer for 2 min. Samples were introduced by pressure injection for 4 s and the separation was performed at 22 kV. Peak integration was done using the Beckman P/ACE Station software. Kinetic parameters were calculated by linear regression from Eadie-Hoftsee plots.

Determination of the Optimal pH and Temperature for Conversion of UDP-GlcNAc by FlaA1:

The pH study was performed in 50 mM sodium acetate buffer at pH 5.0, 5.5, 6.0 and 6.5 as well as in 50 mM Bis-Tris-Propane buffer at pH 6.5, 7.0, 7.5, 8.0, 8.5, 9.0, 9.5 and 10.0. Reactions contained 440 ng of enzyme and 1.5 mM UDP-GlcNAc. They were incubated for 1 h at 37° C.

For the temperature study, reactions also contained 440 ng of enzyme and 1.5 mM UDP-GlcNAc. The buffer was 20 mM Tris pH 7. The reactions were incubated for 1 h on ice or at 15, 20, 30, 37 42, 55 or 65° C.

Functional Characterization of FlaA1 using the GalE Assay

The enzymatic reactions were performed in 20 mM Tris pH 7, with 50 to 300 ng of freshly purified enzyme and 0.8 mM of UDP-Glc or UDP-Gal in a total reaction volume of 44 µl. After incubation for 2 hours at 37° C., the reactions were quenched by acid hydrolysis of the UDP moiety as described above. Standard curves were prepared using UDP-Glc or UDP-Gal that were also subjected to acid hydrolysis. The quantitation of remaining glucose present in the reaction mixture was measured spectrophotometrically as described previously. (Creuzenet et al. 2000) using a coupled assay that is specific for glucose (Moreno et al. 1981). Briefly summarised, a reaction mix containing 22 units/ml of glucose oxidase, 7 units/ml of horse radish peroxidase and 0.3 mg/ml of O-dianisidine was prepared in 50 mM sodium acetate buffer, pH 5.5 400 µl of this reaction mix were added to the neutralised samples described above and the reaction was allowed to proceed for 30 min at 37° C. The reaction was then quenched by addition of 600 µl of 6 N HCl and the optical density at 540 nm was read.

Analysis of the Reaction Products for UDP-Glc and UDP-Gal by Capillary Electrophoresis The same reactions as above were prepared for capillary electrophoresis analysis and were quenched by boiling for 6 minutes without prior acidification. Capillary electrophoresis (CE) analysis was performed as described earlier (Creuzenet et al. 2000).

Mass Spectrometry Analysis of the Reaction Products

Mass spectrometry analysis were performed using a Crystal CE system (APJUNJCAM) directly coupled to a electrospray API3000 mass spectrometry system (Perkin-Elmer). Analysis were performed using a 90 cm long capillary type in 30 mM morpholine buffer at pH 9, under 30 kV. Samples were injected for 0.1 min under 100–150 mbar pressure. Mass spectrometry acquisitions were done in the negative mode with acquisition between m/z=50 and 1200.

Chemical Reduction Experiment:

Reactions (35 µl) containing 440 ng of enzyme and 1.5 mM UDP-GlcNAc in 20 mM Tris pH 7 buffer were incubated for 2 h at 37° C. Serial dilution of sodium borohydride at 10, 1 and 0.1 mg/ml were prepared. One µl of each serial dilution was added to a 35 µl reaction mix and incubated for 15 min at 37° C. The reactions were quenched by boiling for 6 min. The samples were analysed by CE, CE/MS and MS/MS as described above.

Effect of Binding of UDP-Glc or UDP-GalNAc to FlaA1 on the Catalysis of UDP-GlcNAc.

A reaction mix (11×24.5 µl) containing 1.5 mM of UDP-Glc or UDP-GalNAc (or none) and 440 ng of FlaA1 in 20 mM Tris buffer pH 7, was incubated at 37° C. for 45 min. 10.5 µl of serial dilutions of UDP-GlcNAc ranging from 0.02 to 1.50 mM were added to this reaction mix and the reaction was allowed to proceed for 35 min at 37° C. The reaction were quenched by boiling for 6 min. The samples were analysed by CE and the Eadie-Hoftsee plots were constructed for potential K$_i$ determination.

Results

In Vivo Complemenation of a WbpM Knock-Out Mutant by FlaA1

Figure 4:
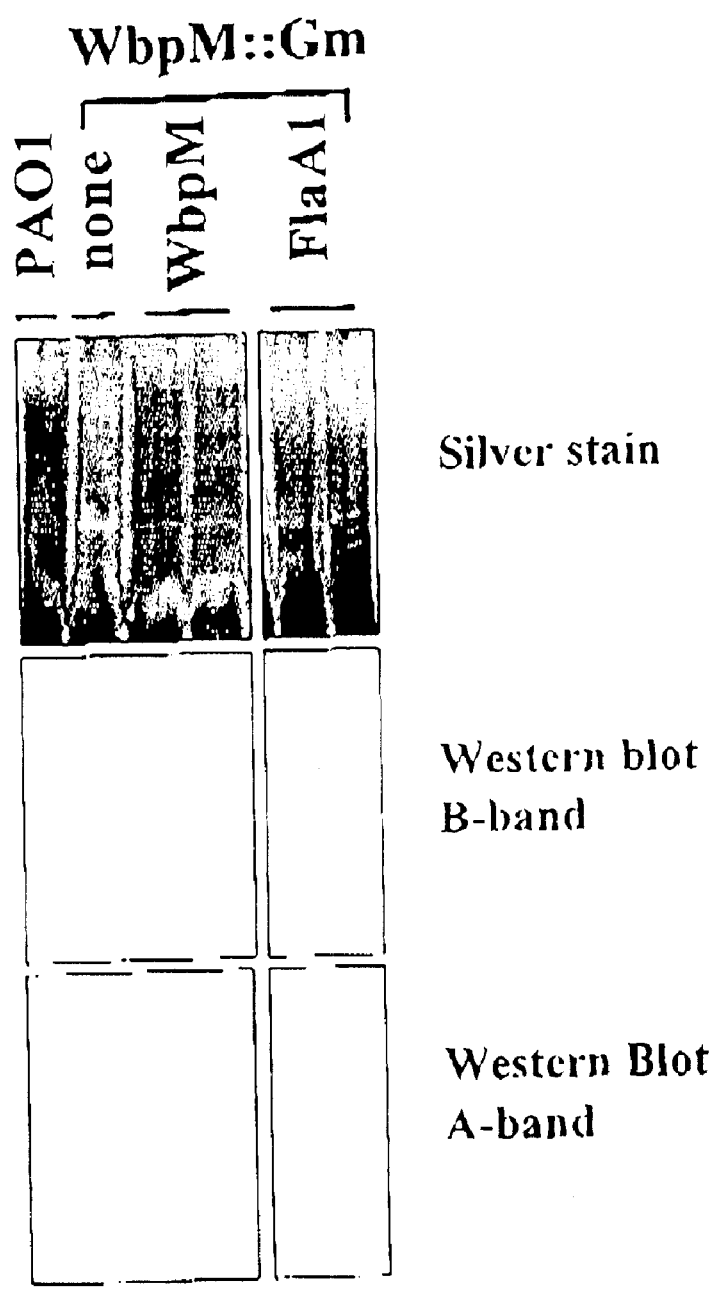
FIG. 4 is an SDS-PAGE analysis of LPS of a WbpM knock-out mutant after complementation by FlaA1.

FIG. 4 shows that the histidine tagged FlaA1 is able to complement a WbpM knock-out and restore the entire ladder-like pattern of B-band LPS that is typical for *P. aeruginosa* serotype. O5. This result confirms that the presence of the N-terminal histidine tag is not deleterious for the function of FlaA1. It also shows that WbpM and FlaA1 are functionally equivalent in contrast to what was observed by Burrows et al 2000.

Figure 5:
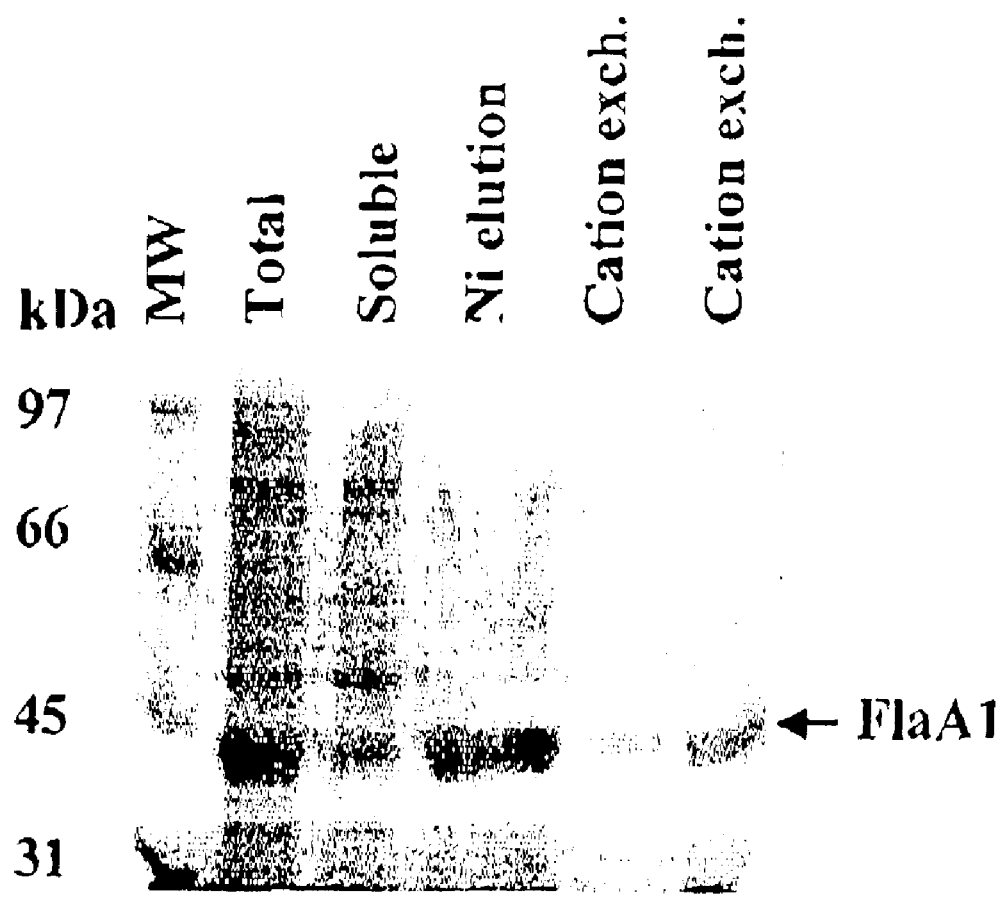
FIG. 5 is an SDS-PAGE analysis of FlaA1 overexpressed in the PET system.

Protein Expression and Purification:

FlaA1 is a small protein (37.4 kDa) of very basic isoelectric point (pI=8.65). It could be overexpressed as a N-terminally histidine-tagged protein in the pET system using E. coli BL21(DE3)pLsS grown in terrific broth. Very high levels (30% of total cell proteins) of expression were obtained provided that fresh transformants were used for each experiment and that the cells were harvested after no more than 5 h or induction. Failure to respect these conditions resulted in important cell death and very poor recovery of FlaA1. 50–60% of the expressed protein was soluble and could be purified to homogeneity by nickel chelation and cation exchange chromatography. FIG. 5 shows the analysis of FlaA1 overexpressed in the pET system by SDS-PAGE. Expression was induced with ImM IPTG in TB at 37° C. Typically, 1.5–2 mg of 95–98% pure FlaA1 could be obtained from 100 ml of culture (Table 3).

Gel filtration chromatography suggests that purified FlaA1 exists as a dimer in native conditions even at low concentration and in the presence of 100 mM NaCl. No bound nucleotide co-factor (NAD(P)+) could be extracted from purified FlaA1 despite numerous attempts using different enzyme preparations and using very concentrated samples.

Figure 6:
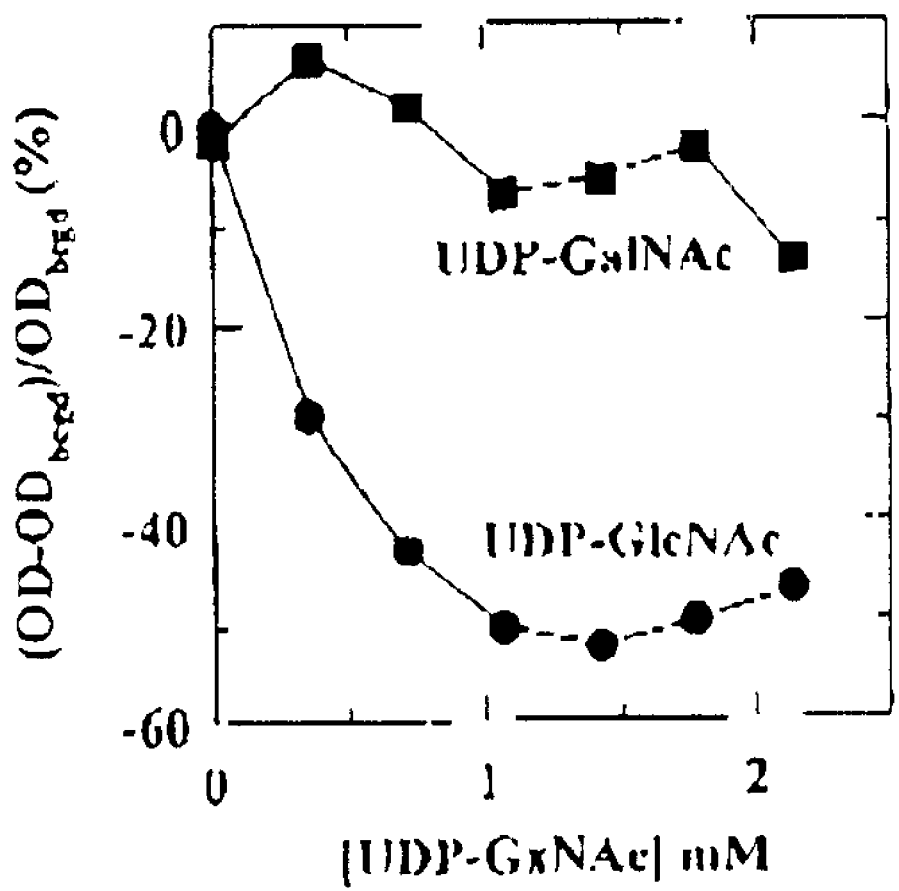
FIG. 6 is a graph showing the FlaA1 modification of UDP-GlcNAc and UDP-GalNAc using DMAB.

Functional Characterization of FlaA1 Using the DMAB Assay:

DMAB is a reagent specific for N-acetyl-hexosamines (Reissig et al 1955). Under the inventors' experimental conditions, it reacts 6 fold more with GlcNAc than with its $C_4$ epimer GalNAc. As adapted by Creuzenet et al 2000, the DMAB assay allows to measure GlcNAc or GalNAc present in an enzymatic reaction by simple measurement of the optical density at 595 nm. When FlaA1 was incubated with UDP-GalNAc, a slight decrease in the $OD_{595nm}$ was observed. The low yield of reactivity of DMAB for UDP-GalNAc and low $OD_{595nm}$ variations observed did not allow precise calculation of the substrate conversion in this case (<5%). However, the assay clearly excludes the existence of a $C_4$ epimerase activity for FlaA1. Such an activity would form UDP-GlcNAc from UDP-GalNAc and would result in a clear increase of $OD_{595nm}$ in the DMAB assay after incubation of FlaA1 with UDP-GalNAc. When the reactions were performed with UDP-GlcNAc, an important decrease in $OD_{595nm}$ was observed. It is dependent on the substrate concentration and amounts to a maximum of 55% substrate conversion under these experimental conditions (FIG. 6). This clearly indicates that UDP-GlcNAc is a good substrate for FlaA1. The disappearance of UDP-GlcNAc is dependent on the amount of enzyme present in the reaction. It is also specific for FlaA1 as indicated by the increased in specific activity (9.9 fold) along the purification (Table 3).

Figure 7:
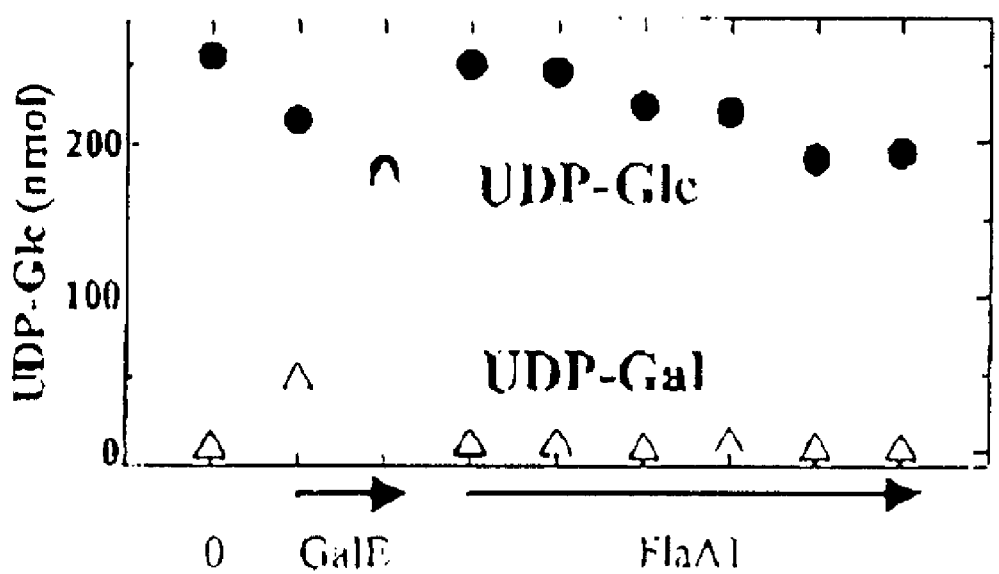
FIG. 7 is a graph showing the FlaA1 modification of UDP-Glc and UDP-Gal using a glucose oxidase based assay.

Functional Characterization of FlaA1 using the GalE Assay:

The GalE assay relies on the use of glucose-specific glucose oxidase and allows to follow UDP-Glc disappearance or appearance when the enzyme assay is performed using UDP-Glc or UDP-Gal, respectively. When the reactions were performed using high amounts of enzyme (300 ng) and low amounts (0.8 mM) of UDP-Glc, a slight disappearance of UDP-Glc that amounted to a maximum of 5% of the substrate was observed (FIG. 7). When the reactions were performed with UDP-Gal, no formation of UDP-Glc was observed. This excludes the existence of $C_4$ UDP-Glc epimerase activity for FlaA1.

Figure 8:
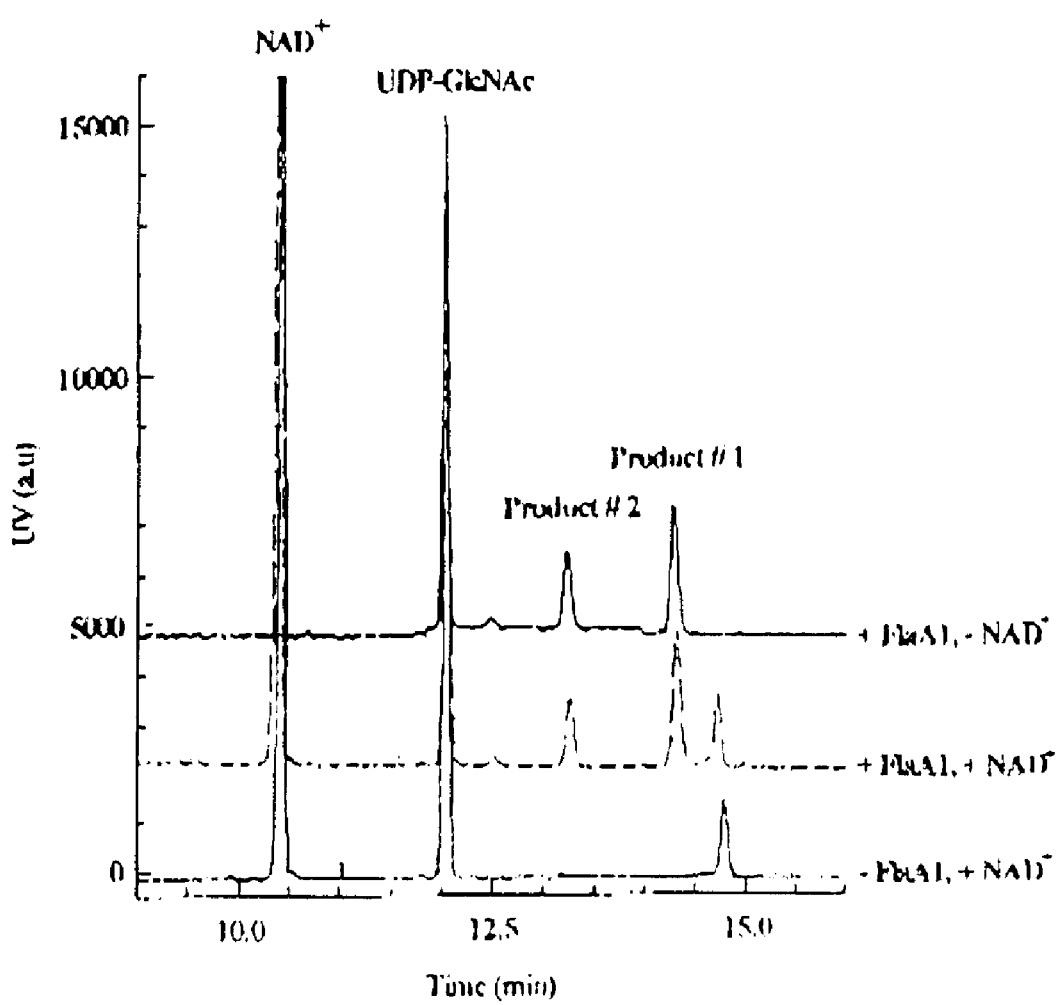
FIG. 8 shows the capillary electrophoresis of the reaction products obtained by modification of UDP-GlcNAc by FlaA1.

Analysis of the Reaction Products by Capillary Electrophoresis:

When reactions were performed using UDP-Glc, UDP-Gal or UDP-GalNAc as substrates, no reaction products could be identified by capillary electrophoresis analysis. However, when UDP-GlcNAc was used as a substrate, two reaction products were identified (FIG. 8). One (Product #1) eluted at 14.5 min and the other (Product #2) eluted at 13.3 min whereas the substrate UDP-GlcNAc eluted at 12 min. As high as 80% substrate conversion could be obtained at equilibrium using 1.5 mM substrate. The percentage of product 2 increased when the total substrate conversion increased whereas that of product 1 reached a maximum. This suggested that product 2 could be a derivative of product 1. A time course experimental performed with very low amounts of enzyme showed that products 1 and 2 appear in a sequential manner. Product 1 is formed first, followed by formation of product 2 once product 1 reaches 5–7% of the substrate. FIG. 8 also shows that no addition of NAD+ is required for UDP-GlcNAc catalysis.

Determination of the Physico-Kinetic Parameters for UDP-GlcNAc by Capillary Electrophoresis:

FlaA1 was active over a broad range of temperature and showed a maximum of activity between 37 and 55° C. Its optimal pH is between 6.5 and 8.0. Consequently, all kinetic analyses were performed at pH 7 and 37° C.

The activity of FlaA1 could be partially preserved by storage at −20° C. in 25% glycerol. However, the rates of the reactions were significantly lower after storage. Consequently, all kinetic data were obtained with freshly purified enzyme.

Time course experiments performed with different substrate concentrations showed that at 20 min, less than 10% of the total substrate is converted and that the reaction is proceeding under initial rates conditions for the range of substrate concentrations chosen. The Km and $V_{max}$ for UDP-GlcNAc determined under these conditions were 0.159 mM and 0.065 nmol/min (Table 4). These numbers refer to total substrate conversion, with appearance of both products 1 and 2. The $k_{cal}$ value was of 5.1 $min^{-1}$.

Potential Inhibitory Effect of the Binding of UDP-Glc or UDP-GalNAc to FlaA1 on the Catalysis of UDP-GlcNAc.

Incubation of UDP-Glc or UDP-GalNAc with FlaA1 before addition of the substrate did not have any inhibitory effect on the catalysis of UDP-GlcNac. The Km and $v_{max}$ of the enzyme for UDP-GlcNAc were not significantly affected.

Figure 9:
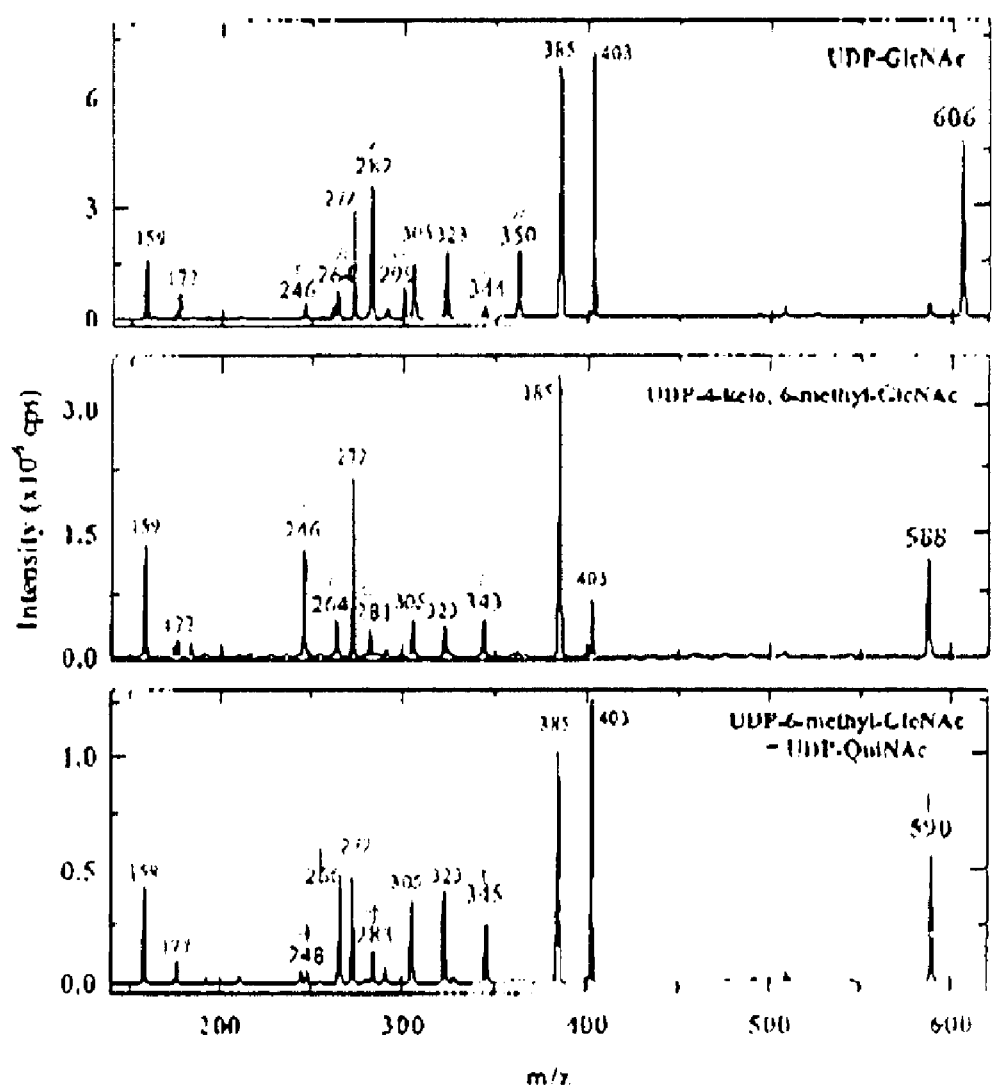
FIG. 9 shows the MS/MS analysis of the reaction products after modification of UDP-GlcNAc by FlaA1.
Figure 10:
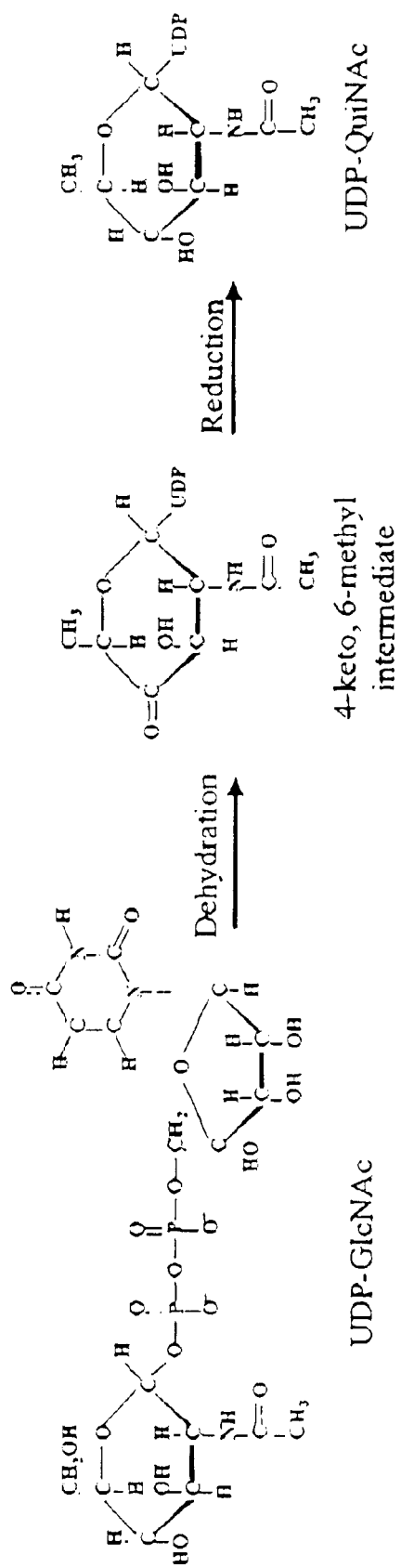
FIG. 10 is a schematic diagram showing the activity of FlaA1 as a UDP-GlcNAc dehydratase/reductase.

Identification of the Products of UDP-GlcNAc Catalysis by Mass Spectrometry:

CE/MS analysis of the reaction mixture showed the appearance of two peaks at m/z 588 and 590 when both products 1 and 2 were formed, and only of one peak at m/z 588 when only product 1 was formed. Hence product 1 is assigned to the peak at m/z 588 whereas product 2 is assigned to the peak at m/z 590. Compared with the substrate peak (m/z 606), these two peaks could correspond to a 4-ket0, 6-methyl derivative of UDP-GlcNAc (m/z 588) and to 6-methyl UDP-GlcNAc also called UDP-QuiNAc (m/z 590) arising from stereospecific reduction of the first product (see FIG. 10). Further analysis of each peak by MS/MS revealed a fractionation pattern consistent with this hypothesis (FIG. 9 and Table 3). In FIG. 9, peaks specific for the parent peak (*), the 4-keto, 6-methyl intermediate (#) or the reduced product (+) are indicated. Several peaks common to the MS/MS map of each parent peak attest for an unaltered structure of the UDP moiety as expected. Others are specific for each parent peak. They attest for the replacement of the CH$_2$OH group (observed in peak at m/z 606) on C$_6$ of the glucose ring by a CH$_3$ group (in peak m/z 588 and 590), and for the replacement of a CHOH group (in peak at m/z 606 and 590) by a C|O group (in peak at m/z 588) on C$_4$ of the glucose ring. They also confirm that the N-acetyl group on C$_2$ of the glucose ring is not affected by the enzymatic reaction. Partial C$_2$ deacetylation occurs during CE/MS, resulting in appearance of parent peaks at m/z 563 (deacetylated UDP-GlcNAc), 545 (deacetylated product 1) and 547 (deacetylated product 2). Their MS/MS fragmentation patterns also match for the enzymatic modifications described above. This confirms further that the acetyl group of the glucose moiety is not involved in the enzymatic reaction. All these results confirm that FlaA1 has a C$_6$ dehydratase activity of UDP-GlcNAc and are consistent with the participation of a 4-keto, 6-methyl intermediate that is further reduced to produce UDP-QuiNAc.

Does FlA1 also Possess Reductase Activity?

To investigate if the reduction of product 1 into product 2 is enzyme-catalysed or results from the reducing power of the Tris buffer used for enzymatic reactions, reactions were performed in several different buffers. The total reaction yields and proportions of product 1 and 2 obtained at equilibrium were not significantly affted by the use of buffers with low or no reducing power such as Bis-Tris-Propane, sodium phosphate or sodium acetate as compared with the results obtained with Tris buffer. This excludes the possibility that the buffer would be responsible for the observed reduction and confirms that FlaA1 also carries the reduction activity.

Is the Reductase Activity of FlaA1 Stereo-Specific?

The enzyme-catalysed reduction of the 4-keto, 6-methyl intermediate is expected to be stereo-specific whereas a chemical reduction due to the buffer or a reducing agent is not. Hence, upon chemical reduction, a third product corresponding to the C$_4$ epimer of UDP-QuiNAc, UDP-FucNAc, is expected to appear. When the reaction mixture was subjected to mild chemical reduction by sodium borohydride (FIG. 9) an additional peak that migrated between products 1 and 2 on CE was observed. Due to the presence of other insaturated bonds in the nucleotide moiety of the products that also react with the reducing agent, significant loss of the total product was observed. However, by adjusting the concentration of reducing agent used, we were able to find conditions where only the reduced product was left (FIG. 9). CE/MS analysis of this product revelaed a peak at m/z 590. Its MS/MS fragmentation pattern was identical to that of the m/z 590 derived from product 2. Since product 2 is not present in the sample analysed, it can be concluded that the reduced product corresponds to the C$_4$ isomer of product 2 and is UDP-FucNAc. This is consistent with a non-stereospecific chemical reduction.

The respective migration times of UDP-QuiNAc and UDP-FucNAc are also consistent with the order of elution observed on CE between the C$_4$ epimers UDP-GlcNAc (11.6 min) and UDP-GalNAc (12.3 min) or UDP-Glc (12.2 min) and UDP-Gal (12.7 min) under the same conditions. This confirms that the keto group was most likely at position 4 initially. From all these results, it can be concluded that FlaA1 also has stereo-specific C$_4$ reductase activity of the 4-keto, 6-methyl intermediate and is globally a bi-functional C$_6$ dehydratase/C$_4$ reductase that converts UDP-GlcNAc into UDP-QuiNAc via formation of a 4-keto, 6-methyl intermediate.

The inventors results from in vivo complementation of a WbpM knock-out by FlaA1 in *P. aeruginosa* strongly suggested that FlaA1 was a dehydratase. This was confirmed by their biochemical study that not only excluded a C$_4$ epimerase activity but also proved the existence of C$_6$ dehydratase activity. The inventors' positive complementation result also confirms that the N-terminal histidine tag does not interfere with the activity of FlaA1. It also confirms the hypothesis apparent from the MAST/MEME domain analysis that the C-terminal half of large homologues represents the catalytic domain of the proteins. The membrane domains and extra linker domain found in these homologues must play a structural role or be responsible for subtle differences in terms of substrate specificity and/or physico-kinetic properties of the enzymes that are not apparent by complementation analysis.

To the inventors' knowledge, no UDP-GlcNAc dehydratase has ever been studied at the biochemical level. Most studies on sugar-nucleotide dehydratases have focused on GDP-D-mannose and dTDP- or CDP-D-glucose dehydratases.

FlaA1 is very specific for UDP-GlcNAc and can not proceed to catalysis with closely related substrates such as UDP-Glc, UDP-GalNAc and UDP-Gal. Absence of catalysis was also observed with dTDP-D-glucose and GDP-mannose. This, together with the low level of sequence homology observed between FlaA1 and all other known dehydratases confirms that FlaA1 belongs to a separate biosynthetic pathway. The segregation of biosynthetic pathways within the cell via high substrate specificity of enzymes is an efficient mechanism that allows light regulation of specific functions as a response to environmental stimulus. This is particularly important for enzymes involved in virulence factor production like sugar-nucleotide dehydratases, since the pattern of virulence factor expression is usually finely regulated during host colonisation (McGroarty and Rivera 1990, Cruzenet et al. 1990).

The purified FlaA1 was found to exist as a dimer in its native form. This is consistent with the results obtained for the above-mentioned dehydratases whose oligomerisation status has been characterised by gel filtration chromatography. The only exception is *E. coli* GMD which has been found to exist as an hexamer (Tonetti et al 1998).

By analogy to C$_4$ epimerases (Frey 1996 FASEB, Thoden et al. 1996) the reaction mechanism for dehydrates is considered to involve the formation of a 4-keto intermediate and result in the production of a 4-keto, 6-methyl derivative of the substrate. The involvement of a nucleotide cofactor (NAD$^{30}$ for dTDP- or CDP-D-glucose dehydratases and NADP$^+$ for GMD) suggests a hydride transfer mechanism similar to that described for epimerases. In this mechanism, the cofactor NAD(P)$^+$ is considered to be a catalytic prosthetic group rather than a co-substrate contrarily to what is observed in most NAD(P)$^+$-dependent enzymes (He et al. 1996; Liu and Thorson 1994). In the case of C$_4$ epimerases like GalE, the glucose ring is deprotonated at the C$_4$ position via proton transfer to NAD(P)$^+$ to form the 4-keto intermediate. Since the substrate is only maintained within the active site via its nucleotide moiety and freely rotates around the bond between P$_\beta$ of UDP and O of the pyranosyl ring (Frey 1996), reprotonation at C$_4$ can occur on either side of the glucose ring and results in a non-stereospecific epimerisation of the substrate. In dehydratases, however, isotopic labelling experiments (Snipes et al. 1997) have shown that the proton that has been removed from C$_4$ is transferred in a stereospecific manner from the cofactor to the C$_6$ position of the hexose ring after dehydration. This results in the formation of a 4-keto, 6-methyl derivative of the substrate. This suggests the existence of additional anchorage points of the sugar moiety of the substrate in the active site. This is consistent with the high substrate specifically observed with FlaA1 for UDP-GlcNAc as opposed to other UDP-bound sugars. The specificity for the $C_2$-N-acetylated and $C_4$-glucose epimer suggests the existence of interactions of specific residues of FlaA1 with the $C_4$ hydroxyl group and $C_2$ N-acetyl sbustituting group. The determination of the structure of FlaA1 and of the closely related $C_4$ epimerase WbpP in the presence of their common substrate UDP-GlcNAc is under investigation using crystallographic methods to address this possibility.

Surprisingly, despite numerous attempts using a method that allowed readily extraction of NAD(P)$^+$ from the closely related epimerase WbpP, we were unable to demonstrate the existence of any bound nucleotide cofactor in FlaA1. MALD1-TOF mass spectrometry analysis confirmed this result. However there was no requirement for additional NAD(P)$^+$ to obtain full activity of FlaA1. Hence, no nucelotide cofactor seems to be involved in the catalysis of UDP-GlcNAc by FlaA1. This is in contrast to what is observed for $C_4$ epimerases and other dehyratases as described above. This suggests a potentially different catalytic mechanism for FlaA1. A mechanism by direct carbon-carbon bond cleavage rather than deprotonation/reprotonation has been proposed for the NAD$^+$-independent L-ribulose-5-phosphate 4-epimerase (Johnson and Tanner, 1998 biochemistry). However, it doesn't seem suitable either in the case of FlaA1 because it is inconsistent with the existence of a 4-keto intermediate form. Site-directed mutagenesis and structural studies of FlaA1 have been initiated to detect important catalytic residues and ultimately propose a catalytic mechanism that could be tested enzymatically.

Because 4-keto intermediates are unstable molecules (Bonin et al. 1997; Ohyama et al. 1998), their existence has only been demonstrated directly in a few instances (Sullivan et al. 1998; Yoshida et al. 1999). In the case of FlaA1, using the strong resolution and analytical power of CE and MS, we were able to provide direct evidence for the existence of a 4-keto, 6-methyl intermediate and follow the kinetics of its appearance. It should be noted that MS data alone can not unambiguously exclude the formation of a $C_3$ keto intermediate instead of a $C_4$ keto one. The presence of both keto forms has actually been observed in the case of human GDP-mannose dehydratase but the authors (Sullivan et al. 1998) acknowledged that the presence of the $C_3$ keto form could arise from processing of the compounds before analysis. Our results show a strong selectivity for the $C_4$ epimer UDP-GlcNAc as opposed to UDP-GalNAc, hence suggesting participation of the $C_4$ hydroxyl into the chemical reaction rather than $C_3$ group.

For all known 4,6-dehydrateses, the final reaction product is the 4-keto, 6-methyl derivative of the substrate. It is further modified by other enzymes of the relevant biosynthetic pathway by reduction, epimerisation or dehydration. For example, RmlC (Stern et al. 1999), CDP-6-deoxy-1-threo-D-glycero-4-hexulose-3-dehydrase (Thorson et al. 1994) and GMER (Somers et al. 1996, Rizzi et al. 1998) perform the subsequent modification in the dTDP-D-glucose, CDP-D-glucose and GDP-D-mannose pathways, respectively. In contrast to all other dehydratases known to date, FlaA1 is bi-functional and carries out a subsequent reduction of the UDP- 4-keto, 6-methyl GlcNAc into UDP-QuiNAc. CE and MS/MS analyses showed that the enzyme-catalysed reduction is stereospecific whereas the chemically-catalysed reduction is not and leads to the formation of a mixture of UDP-QuiNAc and UDP-FucNAc. Hence, our results show that FlaA1 shares with $C_4$ epime-rases and other sugar-nucleotide dehyratases some common aspect of the reaction mechanism that involves the formation of a 4-keto intermediate. However, the enzyme further modifies the substrate by stereospecific $C_4$ reduction of the 4-keto intermediate after $C_6$ dehydration has been completed.

FlaA1 has a similar affinity for UDP-GlcNAc than the $C_4$ epimerase WbpP (Km 0.22 mM) (Creuzenet et al. 2000), but the catalysis proceeds much slower (50 fold) for FlaA1 as indicated by the low $k_{cat}$ value. This is probably the result of the dehydratase carrying two independent functions at two positions of the substrate molecule as opposed to $C_4$ epimerisation that only involves the $C_4$ position of the substrate. Kinetic parameters are only available for a few other dehydratases. The Km reported for human and E. coli GDP-mannose dehydratases for their substrate are 80 and 260 $\mu$M (Sullivan et al. 1998) and the Km for dTDP-glucose dehydratases are 31–35 $\mu$M (Vara and Hutchinson 1988; Thompson et al. 1992). Though these values are of the same order of magnitude as what we found for FlaA1, none of these enzymes exhibit a bi-functional character like FlaA1 and this introduces a bias in the comparison of kinetic data.

To our knowledge, this paper is the first report of a complete kinetic and mechanistic analysis for a bi-functional UDP-GlcNAc $C_6$ dehydratase/$C_4$ reductase. FlaA1 can now be used routinely to produce UDP-QuiNAc. Since the unavailability of substrates is a limiting step for the study of sugar-nucleotide modifying enzymes, the identification and characterization of the reaction products of FlaA1 with UDP-GlcNAc now open the way to the study of other biosynthetic enzymes that use these products as substrates. It also clarifies ambigous functional assignments previously made for biosynthetic pathways where homologues of FlaA1 exist.

Example 2

Purification of Guanidine Soluble WbpMΔ1-132 Overexpressed in the pET System

Figure 17:
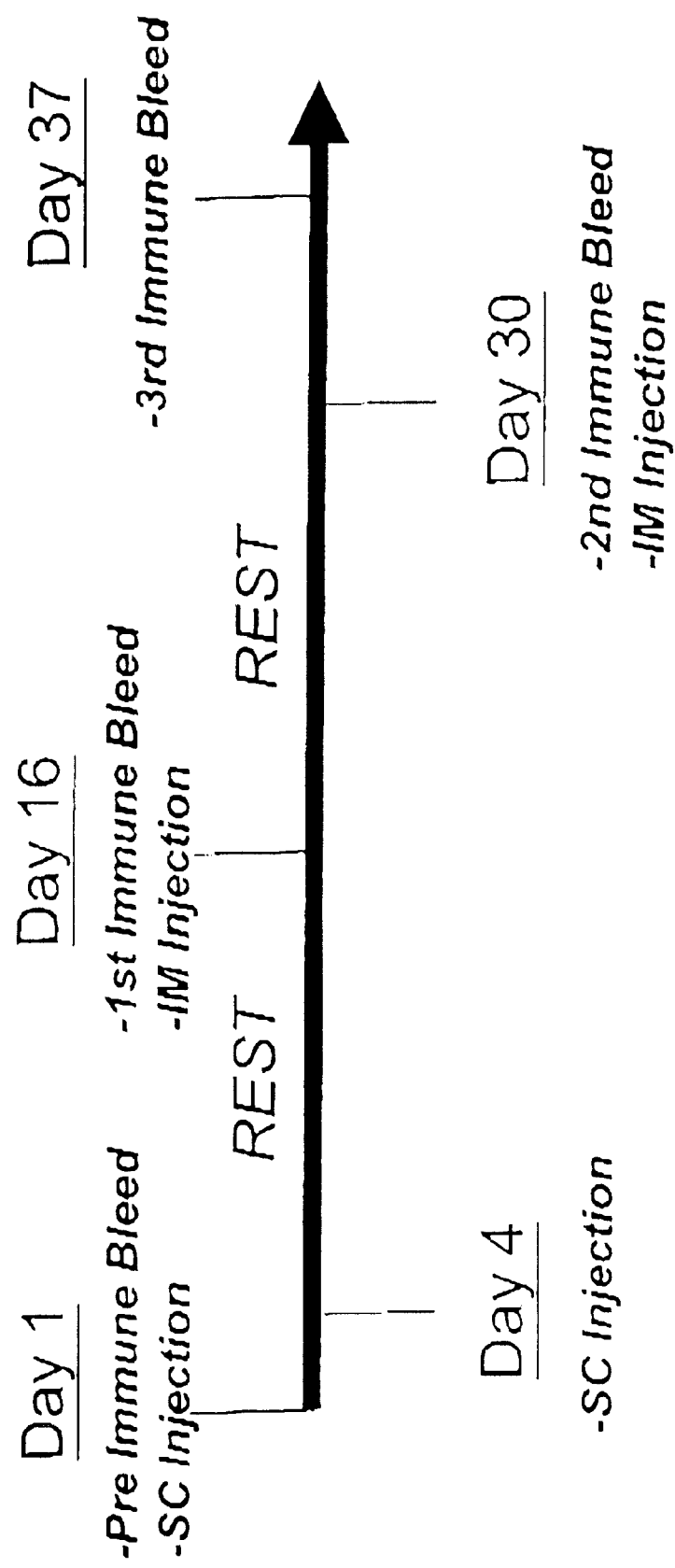
FIG. 17 shows the schedule for immunization and serum collection to raise anti WbpMΔ1-132 in rabbits.

The cell lysis was performed the same way as for FlaA1 (see Example 1) and the inclusion bodies containing WbpMΔ1-132 were solubilized in 6 M guanidine (Gdn-HCl). Purification was performed like for FlaA1 except that all buffers were supplemented with 6 M Gdn-HCl. The purified fraction was dialysed against 3×21 of 10 mM Tris pH 8. The precipitated protein was resuspended in SDS-PAGE loading buffer and run on SDS-PAGE gels. The gels were negatively stained with zinc (Hardy et al. 1996) and the band containing WpbMΔ1-132 was excised. The protein was recovered from the gel by electroelution (BioRad), dialyzed against water and lyophilized. A yield of 1.2 mg of pure WbpMΔ1-132 was recovered from 100 ml of culture.
Rabbits Immunization for the Production of Anti-WbpMD-132 Antiserum:
Immunization and Serum Preparation:

Two female New Zealand White rabbits were used to produce a polyclonal antiserum to the WpbM Δ1-132 protein. The immunizing dose (per rabbit) consisted of 150 $\mu$g of pure WbpMΔ1-132 protein (in a volume of 250 $\mu$l) emulsified in a 1:1 ratio with Freund's Incomplete Adjuvant (Difco), resulting in a total volume of 500 $\mu$l with a 0.85% (w/v) saline concentration. A pre-immunization control serum was collected from each rabbit before commencing immunization. Sub-cutaneous (SC) injections were administered on Day 1 and Day 4, followed by intramuscular (1M) injections on Day 16 and Day 30 (FIG. 17). Test bleeds to monitor the progression of the immune response were collected on Day 16 (1st immune serum), 30 (2nd immune serum), 37 (3rd immune serum). The collected blood was incubated 1 h at room temperature, 30 min at 37° C. and finally 30 min at 4° C. to allow cloning of blood cells. The serum was separated from the clot by centrifugation at 1100× g for 10 min, and the supernatant was collected and stored at −20° C.

Determination of Antiserum Titer by Enzyme-Linked Immunosorbent Assay:

170 ng of WbpMΔ1-132 protein was immobilized onto each well of a Immulon II 96-well microtitration plate (Dynatech Laboratories) by an overnight incubation at 37° C. The wells were washed with PBS containing 0.05% Tween 20, blocked for 1 h at 37° C. with 3% BSA in the same buffer and washed again. Serial ten-fold dilutions of crude rabbit antiserum (from $1\times10^{-1}$ to $1\times10^{-8}$) were added to the wells in triplicates and were incubated for 1 h at 37° C. The wells were washed with PBS/Tween again, and a 1:2000 dilution of goat anti-rabbit IgG alkaline phosphatase conjugated F(ab')$_2$ fragments (Jackson ImmunoResearch Laboratories) was added to each well and incubated for 1 h at 37° C. After a last wash with PBS/Tween, 0.1% p-nitrophenyl phosphate was added and the $OD_{405nm}$ was recorded after 30 min. The titer is defined as the inverse of the last antiserum dilution giving a positive reaction (ABS>0.1) to 170 ng of WbpMΔ1-132. The specificity of the antiserum for WbpM (or its homologues) was assessed by Western immunoblot using whole cell extracts of *E. coli* overexpressing WbpM (or its homologues) or of PAO1.

Example 3

Preparation of Membranes from *Pseudomonas Aeruginosa* Serotypes O5 (PAO1)

Cells were sedimented by centrifugation at 2500× g from a 100 ml overnight culture in LB and resuspended in 10 ml of 50 mM Tris pH 8, 2 mM EDTA. Lysozyme was added at a concentration of 0.1 g/l and lysis was allowed to proceed at 30° C. for 30 min. DNaseI and MgCl$_2$ were added to a final concentration of 0.05 g/l and 1 mM respectively, and incubation was allowed to continue for 15 min. Cell debris were removed by centrifugation at 13 00× g for 15 min, and membranes were separated from the soluble components by centrifugation at 210 00× g for 45 min. The membranes were resuspended in 0.5 ml of 50 mM Tris pH 8, 2 mM EDTA. The presence of WbpM in the membranes was investigated by SDS-PAGE analysis and Western immunoblot using the anti-WbpMΔ1-132 antibody. The purity of the membranes was assessed by Western immunoblot using a DIG-labeled anti-CAT antibody. The purpose of using these membrane preparations was to compare native and overexpressed WbpM to confirm their correct structure and function.

Example 4

Overexpression of WbpM05, WbpMΔ1-132 and WbpM06

General Materials and Methods
Materials:

Two DNA polymerase, Expand long range polymerase and Pwo, as well as calf intestine alkaline phosphatase were from Boehringer-Mannhein. dNTPs were from Perkin Elmer. T4 ligase was from Gibco BRl. The pentaIlis anti histidine tag antibody was from Qiagen. The pET vector was from Novagen, the pBAD24 and pPICZa vectors were from Invitrogen. Luria broth, Terrific broth and Yeast extract and Bactopeptone were from Difco (Detroit, Mich.).

Overpressed of WbpMO5, WbpMA1-132 and WbpM)6 in the pET System:
Cloning:

The genes were amplified by PCR from plasmid pFV169SK (Burrows et al. 1996) for WbpMO5 and its truncated version WbpMA1-132 and from plasmid pFV610-26 (Belanger et al. 1999) for WbpMO6. the DNA and protein sequences for each protein are indicated in FIGS. 11 to 16. The primers and DNA polymerase used are listed in Table 1. The PCR reactions were: 100 ng plasmid, 0.5 $\mu$M each primer, 0.2 mM each dNTP, 4 mM MgCl$_2$ (total) and 1× buffer in a total of 50 $\mu$l when Pwo was used, and 100 ng plasmid, 0.5 $\mu$M each primer, 0.35 mM each dNTP and 1× buffer#1 in a total of 50 $\mu$l when Expand was used. A 5 min denaturation at 94° C. was done before addition of polymerase (1.5 untis of Pwo, or 2.5 units of Expand). This was allowed by 15 cycles of 1 min at 94° C., 45 sec at 40° C. and 90 sec at 72° C. for Pwo or 68° C. for Expand. A final 7 min elongation was performed at 72° C. for Pwo or 68° C. for Expand. The PCR products were digested with restriction enzymes AFIII and BamHI and cloned into the NcoI/BamHI of a derivative of the pET23a that allows in frame cloning with a N-terminal hexahistidine tag (Newton and Mangroo, 1999). The ligation was done with T4 ligase for 12 h at 12° C. and the ligation mix was transferred into CaCl$_2$ competent DH5α cells with 100 $\mu$g/ml of ampicillin selection. The constructs were checked by restriction analysis and sequencing.

Overexpression

The constructs were transformed into *Escherichia coli* expression strain DL21DE3pLysS. For expression of the proteins, an overnight culture was diluted ⅟₅₀ in fresh LB (Luria broth) or TB (terrifc broth) containing 100 $\mu$g/ml of ampicillin and 34 $\mu$g/ml of chloramphenicol and grown at 37° C. until the $OD_{600nm}$ reached 0.6. Expression was induced by addition of 1 mM lPTG for 3 h. The cells were sedimented by centrifugation at 2500× g and the pellets were kept frozen at −20° C. until needed. Expression was monitored by SDS-PAGE analysis, with Coomassie staining or Western immunoblot using a mouse anti-histidine tag antibody or a rabbit anti-WbpMΔ1-132 antibody.

Overexpression in Yeast *Pichi pastoris:*
Cloning of WbpM in PPICZa:

The gene encoding WbpM with a N-terminal histidine tag was amplified by PCR from the pET23 construct. The primers used are indicated in Table 1. PCR reactions and cycles were as described for cloning in the pET vector, except that the annealing temperature was 60° C. The PCR product was cleaved with restriction enzymes SfuI and EcoRI and cloned into pPICZa that had been cleaved with the same enzymes and treated with alkaline phosphatase. The ligation was done with T4 ligase for 12 h at 12° C. and the ligation mix was transferred into CaCl$_2$ competent Top10F' cells. Transformants were selected for tetracyclin (10 $\mu$g/ml) and Zeocin (25 $\mu$g/ml) resistance. The construct was checked by restriction analysis and sequencing. The construct was linearized with *PmeI* before transfomration in yeasts by electroporation.

Preparation of Electrocompetent Yeasts and Electroporation:

Electrocompetent *Pichia pastoris* strains X-33 and Km-71 were prepared following a modified method of Schiestl et al. 1993. Briefly summarized, a culture was grown overnight in YPD (1% yeast extract, 2% bactopeptone, 2% glucose) at 30° C. and diluted ⅟₃₀ in 50 ml fresh YPD. When the cell density reached an $OD_{600nm}$ of 0.6, the cells were sedimented by centrifugation at 3700× g for 15 min at 4° C., and washed twice with sterile water.

They were resuspended in 900 µl of TE (pH 7.5) and 100 µl of 1 M lithium acetate was added. After 30 min incubation at 30° C. 125 µl of 1 M DTT were added and incubation was continued for 10 min. The cells were then washed twice with sterile water and twice with 1 M cold sorbitol. They were finally resuspended in an equal volume of 1 M cold sorbitol and used immediately for electroporation. For electroporation, 100 µl of electrocompetent yeasts were mixed with 8.5 µg of linearized plasmid contained in 5 µl of water. The electroporation parameters were 1.5 kV, 25 µF and 200 Ohms (Biorad). The electroporation cells were resuspended in 300 µl cold 1 M sorbitol, and allowed to recover unshaken for 90 min at 30° C. They were plated on YDP containing 1 M sorbitol and 100 µg/ml zeocin. Colonies appeared on the plates after 24 h at 30° C. and could be picked after 60 h to be restreaked on YPD/zeocin.

Expression of WbpM in Yeast:

Expression assays were carried out in 1.5 ml minimal glycerol media (MGM) containing 1.34% YNB, 1% glycerol, 4×10F$^{-5}$% biotin, and supplemented with 0.004% histidine for Km-71 cells. When the cell density reached an $OD_{600nm}$ of 2, the cells were sedimented by centrifugation at 1500× g for 5 min at room temperature and the media was replaced with minimal methanol media (MM) containing 1.34% YNB, 0.5% methanol, 4×10E$^{-5}$% biotin, and supplemented with 0.004% histidine for Km-71 cells. Induction was carried out for 6 days at 30° C., with addition of methanol to 0.5% every 24 h. Expression was detected by SDS-PAGE analysis and Western immunoblot using the anti histidine tag antibody or the anti-WbpMΔ1-132 antibody (see Example 2 for the description of antibody production).

Overexpressing of WbpM in pBAD System:

Cloning:

The gene encoding for WbpM with a N-terminal histidine tag was amplified by PCR from the pET23 contstruct. The primers used are indicated in Table 1. The PCR was performed with Expand polymerase in the same conditions as reported for cloning in the pET vector, but the annealing temperature was 60° C. The PCR product was cut with AflIII and HindIII and cloned into pBAD24 that had been cut with the same enzymes and treated with alkaline phosphatase. The ligation was done with T4 ligase and the ligation mix was transferred to CaCl$_2$ competent DH5α and plated on LB containing 0.2% glucose and 100 µg/ml of ampicillin selection. The construct was checked by restriction analysis and sequencing.

Expression:

For expression of the protein, an overnight culture (in *E. coli* DH5α) was diluted 1/50 in fresh LB containing 0.2% glucose and 100 µg/ml of ampicillin and grown at 37° C. until the $OD_{600nm}$ reached 0.6. The cells were sedimented by centrifugation at 2500× g and resuspended in LB containing 0.0002 to 0.2% arabinose and 100 µg/ml of ampicillin. The cells were grown at 37° C. for 3 h and sedimented by centrifugation at 2500× g. The pellets were kept frozen at −20° C. until needed and expression was monitored by SDS-PAGE analysis as described for expression in the pET system.

Purification of detergent soluble WbpM overexpressed in the pBAD system:

The purification was performed the same ways as for FlaA1 except that all buffers were supplemented with 0.1% of Triton X100.

Enzymatic assay for the modification of UDP-GalNAc and UDP-GlcNAc:

Reactions were carried out with 3.5, 7 or 10.5 µl of cell extract or purified protein prepared as described above under General Materials and Methods, in a 35 µl total volume of Tris 20 mM pH 8, NAD' 1 mM, UDPGalNAc or UDPGlcNAc 1 mM, CaCl$_2$ 4 mM, MgCl$_2$ 4 mM and MnCl$_2$ 4 mM. After 2 h incubation at 37° C., the reactions were stopped by addition of 7 µl of HCl 0.1N, boiled for 15 min, and neutralized by addition of 7 µl of NaOH 0.1N. Control reactions were performed without enzyme or cell extract, as well as with extracts of induced cells harboring the pET23 vector only (no gene expressed).

Spectrophotometric quantification of UDP-GalNAc and UDP-GlcNAc:

The quantification of UDP-GalNAc and UDP-GlcNAc was carried out spectrophotometrically using p-dimethylaminobenzaldehyde (DMAB) using a modified procedure from Reissig et al 1955. The reagent was prepared at 10% in glacial acetic acid/HCl 9/1 v/v, and further diluted 1/10 in glacial acetic acid before use. For the assay itself, 100 µl of 0.2 M sodium tetraborate pH 9.1 were added to 50 µl of quenched and neutralized enzymatic reactions and boiled immediately for 3 min. 40 µl of this mixture were transferred to a microtitration plate and 200 µl of DMAB reagent was added. After incubation for 90 min at room temperature the $OD_{595\ nm}$ was recorded. The assay was done in duplicate for each enzymatic reaction tested. For practical reasons, the DMAB assay is carried out using a wavelength setting of 595 nm in the spectrophotometer. However, the signal of the assay could be increased by approximately 15% if the wavelength is adjusted to 580 nm.

The results of the experiment demonstrate that the spectrophotometric assay has a strong discriminatory power between the two substrates that we are interested in UDP-GalNAc and UDP-GlcNAc even at very low concentrations, and that the yields of reactions are perfectly additive. Hence, if a standard curve is measured for each substrate, the composition of any mixture of both compounds can be determined by linear combination of the standard curves. This is an important feature to be able to quantify the enzymatic conversion of the substrates.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Primers, annealing temperature and DNA polymerase used for PCR amplification and cloning of different proteins in different vectors. Restriction sites are indicated in bold letters. WbpMΔ1—132 designates a deletion from amino acid 1 to amino acid 132 in WbpM05.

| Protein (vector) | Primers | annealing temperature | DNA polymerase |
|---|---|---|---|
| WbpMO5 (pET23) | Top 5'ACTGTACATGTCGATGTTGGATAATTTGAGG3' (SEQ.ID.NO.:13)<br>Bot. 5'AATATGGATCCTCAGGGTTCTCGCCGCCTC3' (SEQ.ID.NO.:14) | 45° C. | Pwo |
| WbpMΔ1—132 (pET23) | Top 5'ACTTTACATGTTGCGTCTGGCCATGCG3' (SEQ.ID.NO.:15)<br>Bot. 5'AATATGGATCCTCAGGGTTCTCGCCGCCTC3' (SEQ.ID.NO.:16) | 60° C. | Pwo |
| WbpMO6 (pET23) | Top 5'ACTCTACATGTTGGATAACTTGCGTGGA3' (SEQ.ID.NO.:17)<br>Bot. 5'AATATGGATCCTCAGGGTTCTCGCCGCCTCT3' (SEQ.ID.NO.:18) | 40° C. | Expand |
| FlaA1 (pET23) | Top 5'ACTGTACATGTCAATGCCAAATCATCAAAAC3' (SEQ.ID.NO.:19)<br>Bot. 5'AAGCTGGATCCTCATAATAATTTCAACAAA3' (SEQ.ID.NO.:20) | 40° C. | Expand |
| WbpMO5 (pPICZa) | Top 5'ATCTCTTCGAATATGGACACCACCACCACCACCACGG3' (SEQ.ID.NO.:21)<br>Bot. 5'ACTTGGAATTCAGGGTTCTCGCCGCCTCTGGC3' (SEQ.ID.NO.:22) | 60° C. | Expand |
| WbpMO5 (pBAD24) | Top 5'ACTACATGTCCCACCACCACCACCAC 3' (SEQ.ID.NO.:23)<br>Bot. 5'TAATTAAGCTTTCAGGGTTCTCGCCGCCTC3' (SEQ.ID.NO.:24) | 60° C. | Expand |

TABLE 2

WbpM and its homologues.

| Protein name | Organism | Length (aa)[c] | Putative function | Accession No./(reference) |
|---|---|---|---|---|
| Subfamily 1[a] | | | | |
| WbpM | Pseudomonas aeruginosa serotype O5 | 665 | Fuc2NAc biosynthesis | U50396 (28) |
| WbpM | Pseudomonas aeruginosa serotype O6 | 665 | Fuc2NAc biosynthesis | AF035937 (13) |
| ORF74.5 | Pseudomonas aeruginosa serotype O11 | 665 | Fuc2NAc biosynthesis | U44089, direct submission |
| TrsG | Yersinia enterocolitica serotype O:3 | 638 | galactose modification | S51266 (270) |
| WlbL | Bordetella bronchiseptica | 624 | nucleotide sugar dehydratase/epimerase | AJ007747, direct submission |
| WlbL | Bordetella pertussis | 624 | FucNAcMe biosynthesis | S70683 (2) |
| WlaL | Campylobacter jejuni | 590 | unknown | Y11648 (97) |
| RfbV | Vibrio cholerae serotype O1 | 621 | unknown | Y07788 (83) |
| ORF22-30 | Vibrio cholerae serotype O22 | 646 | unknown | AB012957, direct submission |
| ORF10 | Vibrio cholerae serotype O139 | 646 | epimerase/dehydratase | U47057 (48) |
| CapD | Staphylococcus aureus serotype 1 | 599 | type 1 capsule synthesis | U10927 (185) |
| Cap5D | Staphylococcus aureus serotype 5 | 607 | unknown | U81973 (261) |
| Cap8D | Staphylococcus aureus serotype 8 | 607 | unknown | U73374 (262) |
| LpsB | Rhizobium etli | 683 | dTDP-glucose-4,6-dehydratase | U56723, direct submission |
| WbiI | Burkholderia pseudomallei | 637 | epimerase/dehydratase | AF0064070 (69) |
| TP0077 | Treponema pallidum | 538 | capsular polysaccharide biosynthesis | AE001192 (96) |
| YveM | Bacillus subtilis | 598 | unknown | Z99121 (164) |
| Subfamily 2[b] | | | | |
| HP0840 | Helicobacter pylori | 333 | unknown | AE000595 (287) |
| JHP0778 | Helicobacter pylori | 333 | sugar nucleotide biosynthesis | AE001508 (3) |
| FlaA1 | Caulobacter crescentus | 331 | unknown | U27301, direct submission |
| Cap5E | Staphylococcus aureus serotype 5 | 342 | unknown | U81973 (261) |
| Cap8E | Staphylococcus aureus serotype 8 | 342 | unknown | U73374 (262) |
| protein D | Methanococcus jannaschii | 333 | capsular biosynthetic protein | U67549 (25) |
| CapD | Rickettsia prowazekii | 341 | unknown | AJ235271 (5) |
| KasD | Streptomyces kasugaensis | 329 | NDP-hexose 4,6-dehydratase | AB005901 (124) |
| Gdh | Saccharopolyspora erythraea | 329 | dTDP-D-glucose-4,6-dehydratase | L37354 (187) |
| BbLPS1.16 | Bordetella bronchiseptica | 357 | nucleotide sugar dehydratase/epimerase | AJ007747, direct submission |

[a]Subfamily 1 contains proteins of approximately 600 amino acids in length.
[b]Subfamily 2 contains proteins under 360 amino acids in length.
[c]aa = amino acids

TABLE 3

Purification table for FlaA1 established using the DMAB assay and UDP-GlcNAc as a substrate.

| Fraction | Vol.[1] (ml) | Conc. (g/l) | Prot. (mg) | Purity (% prot) | Units[2] | Specific activity (mU/mg) | Purif. (activity) |
|---|---|---|---|---|---|---|---|
| Total[3]   | 10  | 3.1  | 31  | 30 | 0.46 | 14.8  | 1   |
| Soluble[3] | 10  | 1.7  | 17  | 15 | 0.43 | 25.3  | 1.7 |
| IMAC       | 3.5 | 1.3  | 4.5 | 80 | 0.38 | 84.4  | 5.7 |
| Cation     | 6   | 0.25 | 1.5 | 95 | 0.22 | 147.0 | 9.9 |

[1]The numbers refer to the purification of FlaA1 from 100 ml of culture.
[2]One unit is defined as the amount of protein necessary to catalyse 1 μmol of substrate per min under our experimental conditions.
[3]For the analysis of total cell extracts or soluble fraction, the controls were total cell or soluble fraction obtained with the same cells harbouring an empty copy of the pET vector (no FlaA1).

TABLE 4

Kinetic parameters for FlaA1 and UDP-GlcNAc as determined by capillary electrophoresis.

| Km (mM) | $V_{max}$ (nmol/min) | Enzyme (pmol) | $k_{cat}$ (min$^{-1}$) | $k_{cat}$/Km (mM$^{-1}$ × min$^{-1}$) |
|---|---|---|---|---|
| 0.159 ± 0.015 | 0.065 ± 0.006 | 12.8 | 5.1 ± 0.4 | 31.9 ± 5.9 |

Full Citations for References Referred to in the Specification

Allen, A., and Maskell, D. 1996 The identification, cloning and mutagenesis of a genetic locus required for lipopolysaccharide biosynthesis in *Bordetella pertussis*. Mol. Microbiol. 19:37–52.

Alm, R A, Trust T J., 1999. J. Mol. Med., 77(12):834–846

Altschul, S. F., T. L. Madden, A. A. Schaffer, J. Zhang, Z. Zhang, W. Miller, and D. J. Lipman. 1997. Capped BLAST and PSI-BLAST: a new generation of protein database search programs. Nucelic Acids Res. 25:3389–3402.

Bélanger, M., Burrows, L. L., and Lam, J. S. 1999. Functional analysis of genes responsible for the synthesis of B-band O antigen of *Pseudomonas aeruginosa* serotype O6 lipopolysaccharide. Submitted to Microbiology.

Bonin C P, Potten I, Vanzin G F, Reiter W D., 1997. The MUR1 gene of *Arabidopsis thaliana* encodes an isoform of GDP-D-mannose-4,6-dehydratase, catalyzing the first step in the de novo synthesis of GDP-L-fucose. Proc. Natl Acad Sci USA., Mar. 4, 1994(5):2085–90.

Burrows, L. L., Charter, D. F., and Lam, J. S. 1996. Molecular characterization of the *Pseudomonas aeruginosa* serotype O5 (PAO1) B-band lipopolysaccharide gene cluster. Mol. Microbiol. 22:481–495.

Burrows et al., 2000, Infect. Immun. 68, 931.

Comstock L. E., Johnson, J. A., Michalski, J. M., Morris, J. G., and Kaper, J. B. 1996. Cloning and sequence of a region encoding a surface polysaccharide of *Vibrio cholerae* O139 and characterization of the insertion site in the chromosome of *Vibrio cholerae* O1. Mol. Microbiol. 19:815–826.

Creuzenet, C., Smith, M., and Lam, J. S. (1999) Pseudomonas'99: biotechnology and pathogensis. Abstract #93. Maui, Hi.

Creuzenet et al., 2000, J. Biol. Chem. In pres.

Doig et al., 1996, Mol. Microbiol. 19, 379.

Dunn et al., 1997, Clin. Microbiol. Rev., 10, 720.

Eaton et al., 1992, J. Med. Microbiol. 37, 123.

Fitzsimmons, S. C. 1993. The changing epidemiology of cystic fibrosis. J. Pediat. 122, 1–9.

Frey, P. A. 1996. The Leloir pathway: a mechanistic imperative for three enzymes to change the stereochemical configuration of a single carbon in galactose. FASEB J. 10:461–470.

Graham, 1991, J. Gastroenterol. Hepatol., 6, 105.

Guzman, L. M., Belin, D., Carson, M. J., and Beckwith, J. 1995. Tight regulation, modulation, and high-level expression by vectors containing the arabinose pBAD promoter. J. Bacteriol. 177:4121–4130.

Josenhans et al., 1995, J. Bacteriol. 177, 3010.

Labigne and De Reuse, 1996, Infect. Agents Disease 5, 191.

Leclerc et al., 1998, J. Bacteriol. 180, 5010.

Lin W. S., Cunneen, T., and Lee, C. Y. 1994. Sequence analysis and molecular characterization of genes required for the biosynthesis of type 1 capsular polysaccharide in *Staphylococcus aureus*. J. Bacteriol. 176:7005–7016.

McGroarty and Rivera, 1990. Infect. Immun. April 58(4):1030–1037

Moreno, F., Rodicio, R., and Herrero, P. 1981. A new colorimetric assay for UDP-glucose 4-epimerase activity. Cell. Mol. Biol. 27:589–592.

Muotiala et al., 1992, Infect. Immun. 60, 1714.

Newton and Mangro, 1999. Biochem J., April:339(Pt 1):63–69

Ohyama C, Smith P L, Angata K, Fukuda M N, Lowe J B, Fukuda M., 1998. Molecular cloning and expression of GDP-D-mannose-4,6-dehydratase, a key enzyme for fucose metabolism defective in Lec13 cells. J Biol Chem., June 5;273(23):14582–7.

Peterson, 1991, N. Engl. J. Med. 234, 1043.

Pitt, J. L. 1988 Epidemiological typing of *Pseudomonas aeruginosa*. Eur. J. Clin. Microbiol. Infect. Dis. 7, 238–247.

Rizzi M, Tonetti M, Vigevani P, Sturla L, Bisso A, Flora A D, Bordo D, Bolognesi M., 1998. GDP-4-keto-6-deoxy-D-mannose epimerase/reductase from *Escherichia coli*, a key enzyme in the biosynthesis of GDP-L-fucose, displays the structural characteristics of the RED protein homology superfamily. Structure. November 15; 6(11):1453–65.

Sau, S., and C. Y. Lee. 1996. Cloning of type 8 capsule genes and analysis of gene clusters for the production of different capsular polysaccharides in *Staphylococcus aureus*. J. Bacteriol. 178:2118–26.

Sau, S., N. Bhasin, E. R. Wann, J. C. Lee, T. J. Foster, and C. Y. Lee, 1997. The *Staphylococcus aureus* allelic genetic loci for serotype 5 and 8 capsule expression contain the type-specific genes flanked by common genes. Microbiology. 143:2395–405.

Smoot et al., 1990, Infect. Immun. 58, 1992.

Snipes C E, Brillinger G U, Sellers L, Mascaro L, Floss H G., 1977. Stereochemistry of the dTDP-glucose oxidoreductase reaction. J Biol Chem. November 25;252(22):8113–7.

Somers W S, Stahl M L, Sullivan F X, 1998. GDP-fucose synthetase from *Escherichia coli*: structure of a unique member of the short-chain dehydrogenase/reductase family that catalyzes two distinct reactions at the same active site. Structure. December 15;6(12):1601–12.

Sreekrishna, K., Potenz, R. H., Cruze, J. A., McCombie, W. R., Parker, K. A., Nelles, L., Mazzaferro, P. K., Holden, K. A., Harrison, R. G., Wood, P. J., Phelps, D. A., Hubbard, C. E. and Fuke, M. 1988. High level expression of heterologous proteins in methylotrophic yeast *Pichia pastoris*. J. Basic Microbiol. 28, 265–278.

Stern R J, Lee T Y, Lee T J, Yan W, Scherman M S, Vissa V D, Kim S K, Wanner B L, McNeil M R., 1999. Conversion of dTDP-4-keto-6-deoxyglucose to free dTDP-4-keto-rhamnose by the rmlC gene products of *Escherichia coli* and *Mycobacterium tuberculosis*. Microbiology, March;145(Pt 3):633–71.

Studier, F. W., Rosenberg, A. H., Dunn, J. J., and Dubendorff, J. W. 1990. Use of T7 RNA polymerase to direct expression of cloned genes. Meth. Enzymol. 185:60–89.

Sullivan F X, Kumar R, Kriz R, Stahl M, Xu G Y, Rouse J, Change X J, Boodhoo A, Potvin B, Cumming D A., 1998. Molecular cloning of human GDP-mannose 4,6-dehydratase and reconstitution of GDP-fucose biosynthesis in vitro. J Biol Chem., April 3;273(14):8193–202.

Szymanski et al., 1999, Mol. Microbiol. 32, 1022.

Thompson M W, Strohl W R, Floss H G., 1992. Purification and characterization of TDP-D-glucose 4,6-dehydratase from anthracycline-producing streptomycetes. J Gen Microbiol., April;138 (Pt 4):779–86.

Thorson J S, Kelly T M, Liu H W., 1994. Cloning, sequencing, and overexpression in *Escherichia coli* of the alpha-D-glucose-1-phosphate cytidylyltransferase gene isolated from *Yersinia pseudotuberculosis*. J Bacteriol., April;176(7):1840–9.

Tomb, J. -F., White, O., Kerlavage, A. R., Clayton, R. A., Sutton, G. G., Fleischmann, R. D., Ketchum, K. A., Klenk, H. P., Gill, S., Dougherty, B. A., Nelson, K., Quackenbush, J., Zhou, L., Kirkness, E. F., Peterson, S., Loftus, B., Richardson, D., Dodson, R., Khalak, H. G., Glodek, A., McKenney, K., Fitzegerald, L. M., Lee, N., Adams, M. D., Hickey, E. K., Berg, D. E., Gocayne, J. D., Utterback, T. R., Peterson, J. D., Kelley, J. M., Karp, P. D., Smith, H. O., Fraser, C. M., and Venter, J. C. 1997. The complete genome sequence of the gastric pathogen *Helicobacter pylori*. Nature 388:539–547.

Tonetti M, Sturla L, Bisso A, Zanardi D, Benatti U, De Flora A., 1998. The metabolism of 6-deoxyhexoses in bacterial and animal cells. Biochimie. November;80(11): 923–31. Review.

Vara J A, Hutchinson C R., 1988. Purification of thymidine-diphospho-D-glucose 4,6-dehydratase from an erythromycin-producing strain of *Saccharopolyspora erythraea* by high resolution liquid chromatography. J Biol Chem., October 15;263(29):14992–5.

Virlogeux, I. et la. 1995. Microbiol. 141, 3039–3047.

Warren and Marshall, 1983, Lancet 1:1273.

West, S. E. H., H. P. Schweitzer, C. Dall, A. K. Sample, and L. J. Runyen-Janecky. 1994. Construction of improved Escherichia-Pseudomonas shuttle vectors derived from pUC18/19 and the sequence of the region required for their replication in *Pseudomonas aeruginosa*. Gene 128: 81–86.

West S E, Schweizer H P, Dall C, Sample A K, Runyen-Janecky L J., 1994. Construction of improved Escherichia-Pseudomonas shuttle vectors derived from pUC18/19 and sequence of the region required for their replication in *Pseudomonas aeruginosa*. Gene., October 11;148(1):81–6.

Wilson D. B., and Hogness, D. S. 1964. The enzymes of the galactose operon in *Escherichia coli*. I. Purification and characterization of uridine diphosphogalactose 4-epimerase. J. Biol. Chem. 239:2468–2481.

Yoshida Y, Nakano Y, Nezu T, Yamashita Y, Koga T., 1999. A novel NDP-6-deoxyhexosyl-4-ulose reductase in the pathway for the synthesis of thymidine diphosphate-D-fucose. J Biol Chem., June 11;274(24):16933–9.

Zhang L., Radziejewska-Lebrecht, J., Krajewska-Pietrasik, D., Toivanen, P., and Skurnik, M. 1997. Molecular and chemical characterization of the lipopolysaccharide O-antigen and its role in the virulence of *Yersinia enterocolitica* serotype O:8. Mol. Microbiol. 23:63–76.

We claim:

1. A method for screening for an inhibitor of an enzyme with FlaA1-like activity comprising (a) incubating a test sample containing (i) an enzyme with FlaA1-like activity, (ii) a substance suspected of being an inhibitor of the enzyme; and (iii) UDP-GlcNAc; (b) stopping the reaction; (c) comparing the amount of UDP-GlcNAc in the test sample with the amount in a control sample wherein a decrease in the amount of GlcNAc in the control sample as compared to the test sample indicates that the substance is an inhibitor of the enzyme.

2. A method according to claim 1 wherein determining if there has been a decrease in UDP-GlcNAc is by quantifying the amount of UDP-GlcNAc in the sample.

3. A method according to claim 1 or wherein the quantification of UDP-GlcNAc is by spectrophotometric analysis of reaction products of p-dimethylaminobenzaldehyde and UDP-GlcNAc.

4. A method according to claim 1 wherein determining if there has been a decrease in UDP-GlcNAc is by measuring the optical density of the sample wherein a decrease in optical density indicates that there has been a decrease in UDP-GlcNAc.

5. A method according to claim 4 wherein the optical density is measured at 595 nm.

6. A method according to claim 1 wherein the enzyme is FlaA1.

7. A method according to claim 1 wherein the enzyme is WbpM.

8. A method according to claim 1 wherein the enzyme is BplL, Cap8D or TrsG.

* * * * *

SEQUENCE LISTING

```
<160> NUMBER OF SEQ ID NOS: 24

<210> SEQ ID NO 1
<211> LENGTH: 1035
<212> TYPE: DNA
<213> ORGANISM: Helicobacter pylori

<400> SEQUENCE: 1
atgcaccacc accaccacca cggttccatg tcaatgccaa atcatcaaaa catgctagac      60
aaccaaacga ttttaatcac cggtggcact gggagttttg gcaaatgctt tgttcgtaaa     120
gttttagaca ccaccaacgc taaaaaaatc atcgtttata gccgagatga attgaaacaa     180
agcgaaatgg ccatggaatt taatgatcct agaatgcgtt tttttatcgg cgatgtcagg     240
gatttagagc gcttgaatta cgctttagag ggcgtggata tttgtatcca tgcggccgcg     300
ctcaagcatg tccctatcgc tgaatacaac cccctagaat gcattaaaac taacattatg     360
ggagcgagca atgtgattaa cgcatgctta aaaaacgcta tcagtcaggt tatcgctcta     420
agcaccgata aagccgctaa ccccattaac ctctacggtg caaccaaatt gtgcagcgac     480
```

-continued

```
aagctctttg tgagtgcaaa caactttaaa ggctcttctc aaacgcaatt tagcgtggtg    540
cgttatggta atgtggtggg gagtcgtggg agcgtggtgc cgttttttaa aaaattagtc    600 caaacaaag cgagtgaaat ccccattacc gatattcgca tgacacgatt ttggatcacc     660
ttagatgagg gggtttcttt tgtgcttaaa agcttgaaaa gaatgcatgg ggggaaatt     720 tttgtgccta aaatccctag catgaaaatg actgatctcg ccaaagccct agcccctaat    780
acccctacta aaatcatagg gattcgtccg ggcgaaaaac tccatgaagt gatgatccct    840
aaagatgaaa gccatttagc cctagaattc gaagactttt tcatcattca gcccaccata    900
agcttccaaa cgcctaaaga ttacacgctc accaaactcc atgaaaaagg ccaaaaagtc    960
gcccctgatt ttgaatacag cagccataat aacaaccaat ggctagagcc tgatgatttg    1020
ttgaaattat tatga                                                    1035
```

<210> SEQ ID NO 2
<211> LENGTH: 344
<212> TYPE: PRT
<213> ORGANISM: Helicobacter pylori

<400> SEQUENCE: 2

```
Met His His His His His Gly Ser Met Ser Met Pro Asn His Gln
1               5                   10                  15

Asn Met Leu Asp Asn Gln Thr Ile Leu Ile Thr Gly Gly Thr Gly Ser
            20                  25                  30

Phe Gly Lys Cys Phe Val Arg Lys Val Leu Asp Thr Thr Asn Ala Lys
        35                  40                  45

Lys Ile Ile Val Tyr Ser Arg Asp Glu Leu Lys Gln Ser Glu Met Ala
    50                  55                  60

Met Glu Phe Asn Asp Pro Arg Met Arg Phe Phe Ile Gly Asp Val Arg
65                  70                  75                  80

Asp Leu Glu Arg Leu Asn Tyr Ala Leu Glu Gly Val Asp Ile Cys Ile
                85                  90                  95

His Ala Ala Ala Leu Lys His Val Pro Ile Ala Glu Tyr Asn Pro Leu
            100                 105                 110

Glu Cys Ile Lys Thr Asn Ile Met Gly Ala Ser Asn Val Ile Asn Ala
        115                 120                 125

Cys Leu Lys Asn Ala Ile Ser Gln Val Ile Ala Leu Ser Thr Asp Lys
    130                 135                 140

Ala Ala Asn Pro Ile Asn Leu Tyr Gly Ala Thr Lys Leu Cys Ser Asp
145                 150                 155                 160

Lys Leu Phe Val Ser Ala Asn Asn Phe Lys Gly Ser Ser Gln Thr Gln
                165                 170                 175

Phe Ser Val Val Arg Tyr Gly Asn Val Val Gly Ser Arg Gly Ser Val
            180                 185                 190

Val Pro Phe Lys Lys Leu Val Gln Asn Lys Ala Ser Glu Ile Pro
        195                 200                 205

Ile Thr Asp Ile Arg Met Thr Arg Phe Trp Ile Thr Leu Asp Glu Gly
    210                 215                 220

Val Ser Phe Val Leu Lys Ser Leu Lys Arg Met His Gly Gly Glu Ile
225                 230                 235                 240

Phe Val Pro Lys Ile Pro Ser Met Lys Met Thr Asp Leu Ala Lys Ala
                245                 250                 255

Leu Ala Pro Asn Thr Pro Thr Lys Ile Ile Gly Ile Arg Pro Gly Glu
            260                 265                 270
```

```
Lys Leu His Glu Val Met Ile Pro Lys Asp Glu Ser His Leu Ala Leu
            275                 280                 285

Glu Phe Glu Asp Phe Phe Ile Ile Gln Pro Thr Ile Ser Phe Gln Thr
        290                 295                 300

Pro Lys Asp Tyr Thr Leu Thr Lys Leu His Glu Lys Gly Gln Lys Val
305                 310                 315                 320

Ala Pro Asp Phe Glu Tyr Ser Ser His Asn Asn Asn Gln Trp Leu Glu
                325                 330                 335

Pro Asp Asp Leu Leu Lys Leu Leu
            340

<210> SEQ ID NO 3
<211> LENGTH: 2031
<212> TYPE: DNA
<213> ORGANISM: Pseudomonas aeruginosa

<400> SEQUENCE: 3
atgcaccacc accaccacca cggttccatg ggcatgttgg ataatttgag gataaagctc      60
ctgggattgc cgcgccgcta taagcgaatg ctgcaagtcc tgccgatgt gactcttgtg     120 tggctatccc tctggctggc tttcttggtc aggttgggca cagaagacat gatcagcccg     180
tttagcggcc atgcctggct gttcatcgcc gccccgttgg tggccattcc cctgttcatc     240
cgcttcggca tgtaccgggc ggtgatgcgc tacctgggca cgacgcccct atcgcgatc      300 gccaaggccg tcaccatttc cgcgctggtc ctgtcgttgc tggtctactg gtaccgctcc     360
ccgccggcgg tggtgccgcg ttccctggtg ttcaactact ggtggttgag catgctgctg     420
atcgcgggct gcgtctggc catgcgccag tatttcatgg gagactggta ctctgctgtg     480
cagtcggtac catttctcaa ccgccaggat ggcctgccca gggtggctat ctatggcgcg     540
ggggcggccg ccaaccagtt ggttgcggca ttgcgtctcg gtcgggcgat gcgtccggtg     600
gcgttcatcg atgatgacaa gcagatcgcc aaccgggtca tcgccggtct gcgggtctat     660
accgccaagc atatccgcca gatgatcgac gagacgggcg cgcaggaggt tctcctggcg     720
attccttccg ccactcgggc ccggcgccga gagattctcg agtccctgga gccgttcccg     780
ctgcacgtgc gcagcatgcc cggcttcatg gacctgacca gcggccgggt caaggtggac     840
gacctgcagg aggtggacat cgctgacctg ctggggcgcg acagcgtcgc accgcgcaag     900
gagctgctgg aacgttgcat ccgcggtcag gtggtgatgg tgaccggggc gggcggctct     960
atcggttcgg aactctgtcg gcagatcatg agttgttcgc ctagcgtgct gatcctgttc    1020
gagcacagcg aatacaacct ctatagcatc catcaggaac tggagcgtcg gatcaagcgc    1080
gagtcgcttt cggtgaacct gttgccgatc ctcggttcgg tgcgcaatcc cgagcgcctg    1140
gtggacgtga tgcgtacctg gaaggtcaat accgtctacc atgcggcggc ctacaagcat    1200
gtgccgatcg tcgagcacaa catcgccgag ggcgttctca caacgtgat aggcaccttg     1260 catgcggtgc aggccgcggt gcaggtcggc gtgcagaact tcgtgctgat ttccaccgac    1320
aaggcggtgc gaccgaccaa tgtgatgggc agcaccaagc gcctggcgga gatggtcctt    1380
caggcgctca gcaacgaatc ggcaccgttg ctgttcggcg atcggaagga cgtgcatcac    1440
gtcaacaaga cccgtttcac aatggtccgc ttcggcaact cctcggttc gtccggttcg     1500 gtcattccgc tgttccgcga gcagatcaag cgcggcggcc cggtgacggt cacccacccg    1560
agcatcaccc gttacttcat gaccattccc gaggcagcgc agttggtcat ccaggccggt    1620
tcgatggggc agggcggaga tgtattcgtg ctggacatgg ggccgccggt gaagatcctg    1680
```

-continued

```
gagctcgccg agaagatgat ccacctgtcc ggcctgagcg tgcgttccga gcgttcgccc    1740
catggtgaca tcgccatcga gttcagtggc ctgcgtcctg gcgagaagct ctacgaagag    1800
ctgctgatcg tgacaacgt gaatcccacc gaccatccga tgatcatgcg ggccaacgag     1860
gaacacctga gctgggaggc cttcaaggtc gtgctggagc agttgctggc cgccgtggag    1920
aaggacgact actcgcgggt tcgccagttg ctgcgggaaa ccgtcagcgg ctatgcgcct    1980
gacggtgaaa tcgtcgactg gatctatcgc cagaggcggc gagaaccctg a             2031
```

<210> SEQ ID NO 4
<211> LENGTH: 676
<212> TYPE: PRT
<213> ORGANISM: Pseudomonas aeruginosa

<400> SEQUENCE: 4

```
Met His His His His His Gly Ser Met Gly Met Leu Asp Asn Leu
1               5                   10                  15

Arg Ile Lys Leu Leu Gly Leu Pro Arg Arg Tyr Lys Arg Met Leu Gln
                20                  25                  30

Val Ala Ala Asp Val Thr Leu Val Trp Leu Ser Leu Trp Leu Ala Phe
            35                  40                  45

Leu Val Arg Leu Gly Thr Glu Asp Met Ile Ser Pro Phe Ser Gly His
    50                  55                  60

Ala Trp Leu Phe Ile Ala Ala Pro Leu Val Ala Ile Pro Leu Phe Ile
65                  70                  75                  80

Arg Phe Gly Met Tyr Arg Ala Val Met Arg Tyr Leu Gly Asn Asp Ala
                85                  90                  95

Leu Ile Ala Ile Ala Lys Ala Val Thr Ile Ser Ala Leu Val Leu Ser
            100                 105                 110

Leu Leu Val Tyr Trp Tyr Arg Ser Pro Pro Ala Val Val Pro Arg Ser
        115                 120                 125

Leu Val Phe Asn Tyr Trp Trp Leu Ser Met Leu Leu Ile Gly Gly Leu
    130                 135                 140

Arg Leu Ala Met Arg Gln Tyr Phe Met Gly Asp Trp Tyr Ser Ala Val
145                 150                 155                 160

Gln Ser Val Pro Phe Leu Asn Arg Gln Asp Gly Leu Pro Arg Val Ala
                165                 170                 175

Ile Tyr Gly Ala Gly Ala Ala Asn Gln Leu Val Ala Ala Leu Arg
            180                 185                 190

Leu Gly Arg Ala Met Arg Pro Val Ala Phe Ile Asp Asp Lys Gln
        195                 200                 205

Ile Ala Asn Arg Val Ile Ala Gly Leu Arg Val Tyr Thr Ala Lys His
    210                 215                 220

Ile Arg Gln Met Ile Asp Glu Thr Gly Ala Gln Glu Val Leu Leu Ala
225                 230                 235                 240

Ile Pro Ser Ala Thr Arg Ala Arg Arg Glu Ile Leu Glu Ser Leu
                245                 250                 255

Glu Pro Phe Pro Leu His Val Arg Ser Met Pro Gly Phe Met Asp Leu
            260                 265                 270

Thr Ser Gly Arg Val Lys Val Asp Asp Leu Gln Glu Val Asp Ile Ala
        275                 280                 285

Asp Leu Leu Gly Arg Asp Ser Val Ala Pro Lys Glu Leu Leu Glu
    290                 295                 300

Arg Cys Ile Arg Gly Gln Val Val Met Val Thr Gly Ala Gly Gly Ser
305                 310                 315                 320
```

-continued

Ile Gly Ser Glu Leu Cys Arg Gln Ile Met Ser Cys Ser Pro Ser Val
            325                 330                 335
Leu Ile Leu Phe Glu His Ser Glu Tyr Asn Leu Tyr Ser Ile His Gln
            340                 345                 350
Glu Leu Glu Arg Arg Ile Lys Arg Glu Ser Leu Ser Val Asn Leu Leu
            355                 360                 365
Pro Ile Leu Gly Ser Val Arg Asn Pro Glu Arg Leu Val Asp Val Met
            370                 375                 380
Arg Thr Trp Lys Val Asn Thr Val Tyr His Ala Ala Tyr Lys His
385                 390                 395                 400
Val Pro Ile Val Glu His Asn Ile Ala Glu Gly Val Leu Asn Asn Val
            405                 410                 415
Ile Gly Thr Leu His Ala Val Gln Ala Ala Val Gln Val Gly Val Gln
            420                 425                 430
Asn Phe Val Leu Ile Ser Thr Asp Lys Ala Val Arg Pro Thr Asn Val
            435                 440                 445
Met Gly Ser Thr Lys Arg Leu Ala Glu Met Val Leu Gln Ala Leu Ser
            450                 455                 460
Asn Glu Ser Ala Pro Leu Leu Phe Gly Asp Arg Lys Asp Val His His
465                 470                 475                 480
Val Asn Lys Thr Arg Phe Thr Met Val Arg Phe Gly Asn Val Leu Gly
            485                 490                 495
Ser Ser Gly Ser Val Ile Pro Leu Phe Arg Glu Gln Ile Lys Arg Gly
            500                 505                 510
Gly Pro Val Thr Val Thr His Pro Ser Ile Thr Arg Tyr Phe Met Thr
            515                 520                 525
Ile Pro Glu Ala Ala Gln Leu Val Ile Gln Ala Gly Ser Met Gly Gln
            530                 535                 540
Gly Gly Asp Val Phe Val Leu Asp Met Gly Pro Val Lys Ile Leu
545                 550                 555                 560
Glu Leu Ala Glu Lys Met Ile His Leu Ser Gly Leu Ser Val Arg Ser
            565                 570                 575
Glu Arg Ser Pro His Gly Asp Ile Ala Ile Glu Phe Ser Gly Leu Arg
            580                 585                 590
Pro Gly Glu Lys Leu Tyr Glu Glu Leu Leu Ile Gly Asp Asn Val Asn
            595                 600                 605
Pro Thr Asp His Pro Met Ile Met Arg Ala Asn Glu Glu His Leu Ser
            610                 615                 620
Trp Glu Ala Phe Lys Val Val Leu Glu Gln Leu Leu Ala Ala Val Glu
625                 630                 635                 640
Lys Asp Asp Tyr Ser Arg Val Arg Gln Leu Leu Arg Glu Thr Val Ser
            645                 650                 655
Gly Tyr Ala Pro Asp Gly Glu Ile Val Asp Trp Ile Tyr Arg Gln Arg
            660                 665                 670
Arg Arg Glu Pro
        675

<210> SEQ ID NO 5
<211> LENGTH: 1632
<212> TYPE: DNA
<213> ORGANISM: Pseudomonas aeruginosa

<400> SEQUENCE: 5
atgcaccacc accaccacca cggttccatg ttgcgtctgg ccatgcgcca gtatttcatg      60

-continued

```
ggagactggt actctgctgt gcagtcggta ccatttctca accgccagga tggcctgccc     120 aggtggcta tctatggcgc ggggcggcc gccaaccagt tggttgcggc attgcgtctc       180
ggtcgggcga tgcgtccggt ggcgttcatc gatgatgaca agcagatcgc caaccgggtc    240
atcgccggtc tgcgggtcta taccgccaag catatccgcc agatgatcga cgagacgggc    300
gcgcaggagg ttctcctggc gattccttcc gccactcggg cccggcgccg agagattctc    360
gagtccctgg agccgttccc gctgcacgtg cgcagcatgc ccggcttcat ggacctgacc    420
agcggccggg tcaaggtgga cgacctgcag gaggtggaca tcgctgacct gctggggcgc    480
gacagcgtcg caccgcgcaa ggagctgctg aacgttgca tccgcggtca ggtggtgatg     540
gtgaccgggg cgggcggctc tatcggttcg gaactctgtc ggcagatcat gagttgttcg    600
cctagcgtgc tgatcctgtt cgagcacagc gaatacaacc tctatagcat ccatcaggaa    660
ctggagcgtc ggatcaagcg cgagtcgctt cggtgaacc tgttgccgat cctcggttcg     720
gtgcgcaatc ccgagcgcct ggtggacgtg atgcgtacct ggaaggtcaa taccgtctac    780
catgcggcgg cctacaagca tgtgccgatc gtcgagcaca acatcgccga gggcgttctc    840
aacaacgtga taggcacctt gcatgcggtg caggccgcgg tgcaggtcgg cgtgcagaac    900
ttcgtgctga tttccaccga caaggcgtg cgaccgacca atgtgatggg cagcaccaag     960
cgcctggcgg agatggtcct tcaggcgctc agcaacgaat cggcaccgtt gctgttcggc    1020
gatcggaagg acgtgcatca cgtcaacaag acccgtttca caatggtccg cttcggcaac    1080
gtcctcggtt cgtccggttc ggtcattccg ctgttccgcg agcagatcaa gcgcggcggc    1140
ccggtgacgg tcacccaccc gagcatcacc cgttacttca tgaccattcc cgaggcagcg    1200
cagttggtca tccaggccgg ttcgatgggg cagggcggag atgtattcgt gctggacatg    1260
gggccgccgg tgaagatcct ggagctcgcc gagaagatga tccacctgtc cggcctgagc    1320
gtgcgttccg agcgttcgcc ccatggtgac atcgccatcg agttcagtgg cctgcgtcct    1380
ggcgagaagc tctacgaaga gctgctgatc ggtgacaacg tgaatcccac cgaccatccg    1440
atgatcatgc gggccaacga ggaacacctg agctgggagg ccttcaaggt cgtgctggag    1500
cagttgctgg ccgccgtgga gaaggacgac tactcgcggg ttcgccagtt gctgcgggaa    1560
accgtcagcg gctatgcgcc tgacggtgaa atcgtcgact ggatctatcg ccagaggcgg    1620
cgagaaccct ga                                                       1632
```

<210> SEQ ID NO 6
<211> LENGTH: 543
<212> TYPE: PRT
<213> ORGANISM: Pseudomonas aeruginosa

<400> SEQUENCE: 6

```
Met His His His His His Gly Ser Met Leu Arg Leu Ala Met Arg
1               5                   10                  15

Gln Tyr Phe Met Gly Asp Trp Tyr Ser Ala Val Gln Ser Val Pro Phe
                20                  25                  30

Leu Asn Arg Gln Asp Gly Leu Pro Arg Val Ala Ile Tyr Gly Ala Gly
            35                  40                  45

Ala Ala Ala Asn Gln Leu Val Ala Ala Leu Arg Leu Gly Arg Ala Met
        50                  55                  60

Arg Pro Val Ala Phe Ile Asp Asp Asp Lys Gln Ile Ala Asn Arg Val
65                  70                  75                  80

Ile Ala Gly Leu Arg Val Tyr Thr Ala Lys His Ile Arg Gln Met Ile
```

-continued

```
                85                  90                  95
Asp Glu Thr Gly Ala Gln Glu Val Leu Leu Ala Ile Pro Ser Ala Thr
                100                 105                 110
Arg Ala Arg Arg Glu Ile Leu Glu Ser Leu Glu Pro Phe Pro Leu
                115                 120             125
His Val Arg Ser Met Pro Gly Phe Met Asp Leu Thr Ser Gly Arg Val
                130                 135                 140
Lys Val Asp Asp Leu Gln Glu Val Asp Ile Ala Asp Leu Leu Gly Arg
145                 150                 155                 160
Asp Ser Val Ala Pro Arg Lys Glu Leu Leu Glu Arg Cys Ile Arg Gly
                    165                 170                 175
Gln Val Val Met Val Thr Gly Ala Gly Gly Ser Ile Gly Ser Glu Leu
                180                 185                 190
Cys Arg Gln Ile Met Ser Cys Ser Pro Ser Val Leu Ile Leu Phe Glu
            195                 200                 205
His Ser Glu Tyr Asn Leu Tyr Ser Ile His Gln Glu Leu Glu Arg Arg
        210                 215                 220
Ile Lys Arg Glu Ser Leu Ser Val Asn Leu Leu Pro Ile Leu Gly Ser
225                 230                 235                 240
Val Arg Asn Pro Glu Arg Leu Val Asp Val Met Arg Thr Trp Lys Val
                245                 250                 255
Asn Thr Val Tyr His Ala Ala Ala Tyr Lys His Val Pro Ile Val Glu
                260                 265                 270
His Asn Ile Ala Glu Gly Val Leu Asn Asn Val Ile Gly Thr Leu His
            275                 280                 285
Ala Val Gln Ala Ala Val Gln Val Gly Val Gln Asn Phe Val Leu Ile
        290                 295                 300
Ser Thr Asp Lys Ala Val Arg Pro Thr Asn Val Met Gly Ser Thr Lys
305                 310                 315                 320
Arg Leu Ala Glu Met Val Leu Gln Ala Leu Ser Asn Glu Ser Ala Pro
                325                 330                 335
Leu Leu Phe Gly Asp Arg Lys Asp Val His His Val Asn Lys Thr Arg
                340                 345                 350
Phe Thr Met Val Arg Phe Gly Asn Val Leu Gly Ser Ser Gly Ser Val
                355                 360                 365
Ile Pro Leu Phe Arg Glu Gln Ile Lys Arg Gly Gly Pro Val Thr Val
370                 375                 380
Thr His Pro Ser Ile Thr Arg Tyr Phe Met Thr Ile Pro Glu Ala Ala
385                 390                 395                 400
Gln Leu Val Ile Gln Ala Gly Ser Met Gly Gln Gly Gly Asp Val Phe
                405                 410                 415
Val Leu Asp Met Gly Pro Pro Val Lys Ile Leu Glu Leu Ala Glu Lys
                420                 425                 430
Met Ile His Leu Ser Gly Leu Ser Val Arg Ser Glu Arg Ser Pro His
                435                 440                 445
Gly Asp Ile Ala Ile Glu Phe Ser Gly Leu Arg Pro Gly Glu Lys Leu
        450                 455                 460
Tyr Glu Glu Leu Leu Ile Gly Asp Asn Val Asn Pro Thr Asp His Pro
465                 470                 475                 480
Met Ile Met Arg Ala Asn Glu Glu His Leu Ser Trp Glu Ala Phe Lys
                485                 490                 495
Val Val Leu Glu Gln Leu Leu Ala Ala Val Glu Lys Asp Asp Tyr Ser
                500                 505                 510
```

Arg Val Arg Gln Leu Leu Arg Glu Thr Val Ser Gly Tyr Ala Pro Asp
            515                 520                 525

Gly Glu Ile Val Asp Trp Ile Tyr Arg Gln Arg Arg Glu Pro
    530                 535                 540

<210> SEQ ID NO 7
<211> LENGTH: 2025
<212> TYPE: DNA
<213> ORGANISM: Pseudomonas aeruginosa

<400> SEQUENCE: 7

| | | | | | |
|---|---|---|---|---|---|
| atgcaccacc | accaccacca | cggttccatg | ttggataact | tgcgtggacg | cctcctggga | 60 |
| ttgccgcgcc | gccagaagcg | cattcttcag | gttgcgacgg | acatcggcct | ggtgtggctt | 120 |
| tcattgtggc | tggctttcct | ggtgcgtctc | ggcaccgaag | acatgatcga | tccgttcggg | 180 |
| gatcacgcct | ggctgttcat | agcggcgcct | ctaaccgcca | tcccgctctt | catccgcttc | 240 |
| ggcatgtacc | gggcggtgat | gcgctacctg | gcaacgacg | cccttatcgc | gatcgccaag | 300 |
| gccgtcacca | tttccgcgct | ggtcctgtcg | ttgctggtct | actggtaccg | ctccccgccg | 360 |
| gcggtggtgc | cccgttccct | ggtgttcaac | tactggtggt | tgagcatgct | gctgatcggc | 420 |
| ggcttgcgtc | tggccatgcg | ccagtatttc | atgggcgact | ggtactctgc | tgtgcagtcg | 480 |
| gtaccatttc | tcaatcgcca | ggatggcctg | ccagggtgg | ccatctatgg | cgcggggcg | 540 |
| gccggcaacc | agttggttgc | ggcattgcgt | ctcggtcggg | cgatgcgtcc | ggtggcgttc | 600 |
| atcgatgacg | acaagcagat | cgccaaccgg | gtcatcgccg | gtctgcgggt | ctataccgcc | 660 |
| aagcatatcc | gccagatgat | cgacgagacg | ggcgcgcagg | aggttctcct | ggcgattcct | 720 |
| tccgccactc | gggcccggcg | ccgagagatt | ctcgagtccc | tggagccgtt | cccgctgcac | 780 |
| gtgcgcagca | tgcctgggtt | catggacctg | ccagcggtc | gggtcaaggt | ggacgacctg | 840 |
| caggaggtgg | acatcgctga | cctgctgggg | cgcgacagcg | tcgcaccgcg | caaggagctg | 900 |
| ctggaacggt | gcatccgcgg | tcaggtggtg | atggtgaccg | gggcgggcgg | ttctatcggt | 960 |
| tcggaactct | gtcggcagat | catgagttgt | tcgcctagcg | tgctgatcct | gttcgagcac | 1020 |
| agcgaataca | acctctacag | catccatcag | gaactggagc | gtcggatcaa | gcgcgagtcg | 1080 |
| ctttcggtga | acctgttgcc | gatcctcggt | tcggtgcgca | atcccgagcg | cctggtggac | 1140 |
| gtgatgcgta | cctggaaggt | caataccgtc | taccatgcgg | cggcctacaa | gcatgtgccg | 1200 |
| atcgtcgagc | acaacatcgc | cgagggcgtt | ctcaacaacg | tgataggcac | cttgcatgcg | 1260 |
| gtgcaggccg | cggtgcaggt | cggcgtgcag | aacttcgtgc | tgatttccac | cgacaaggcg | 1320 |
| gtgcggccga | ccaatgtgat | gggcagcacc | aagcgcctgg | cggagatggt | ccttcaggcg | 1380 |
| ctcagcaacg | aatcggcacc | ggtgctgttc | ggcgatcgga | aggacgtgca | tcacgtcaac | 1440 |
| aagacccgtt | tcaccatggt | ccgcttcggc | aacgtcctcg | gttcgtccgg | ttcggtcatt | 1500 |
| ccgctgttcc | gcgagcagat | caagcgcggc | ggcccggtga | cggtcaccca | cccgagcatc | 1560 |
| acccgttact | tcatgaccat | tcccgaggcg | gcgcagttgg | tcatccaggc | cggttcgatg | 1620 |
| gggcagggcg | gagatgtatt | cgtgctggac | atggggccgc | cggtgaacat | cctggagctc | 1680 |
| gccgagaaga | tgatccacct | gtccggcctg | agcgtgcgtt | ccgagcgttc | gccccatggt | 1740 |
| gacatcgcca | tcgagttcag | tggcctgcgt | cctggcgaga | agctctacga | agagctgctg | 1800 |
| atcggtgaca | acgtgaatcc | caccgaccat | ccgatgatca | tgcgggccaa | cgaggaacac | 1860 |
| ctgagctggg | aggccttcaa | ggtcgtgctg | gagcagttgc | tggccgccgt | ggagaaggac | 1920 |

-continued

```
gactactcgc gggttcgcca gttgctgcgg gaaatcgtca gcggctatgc gcctgacggt   1980
gaaatcgtcg actggatcta tcgccagagg cggcgagaac cctga                  2025
```

<210> SEQ ID NO 8
<211> LENGTH: 674
<212> TYPE: PRT
<213> ORGANISM: Pseudomonas aeruginosa

<400> SEQUENCE: 8

```
Met His His His His His Gly Ser Met Leu Asp Asn Leu Arg Gly
1               5                  10                  15

Arg Leu Leu Gly Leu Pro Arg Arg Gln Lys Arg Ile Leu Gln Val Ala
            20                  25                  30

Thr Asp Ile Gly Leu Val Trp Leu Ser Leu Trp Leu Ala Phe Leu Val
        35                  40                  45

Arg Leu Gly Thr Glu Asp Met Ile Asp Pro Phe Gly Asp His Ala Trp
    50                  55                  60

Leu Phe Ile Ala Ala Pro Leu Thr Ala Ile Pro Leu Phe Ile Arg Phe
65                  70                  75                  80

Gly Met Tyr Arg Ala Val Met Arg Tyr Leu Gly Asn Asp Ala Leu Ile
                85                  90                  95

Ala Ile Ala Lys Ala Val Thr Ile Ser Ala Leu Val Leu Ser Leu Leu
            100                 105                 110

Val Tyr Trp Tyr Arg Ser Pro Pro Ala Val Pro Arg Ser Leu Val
        115                 120                 125

Phe Asn Tyr Trp Trp Leu Ser Met Leu Leu Ile Gly Gly Leu Arg Leu
    130                 135                 140

Ala Met Arg Gln Tyr Phe Met Gly Asp Trp Tyr Ser Ala Val Gln Ser
145                 150                 155                 160

Val Pro Phe Leu Asn Arg Gln Asp Gly Leu Pro Arg Val Ala Ile Tyr
                165                 170                 175

Gly Ala Gly Ala Ala Gly Asn Gln Leu Val Ala Ala Leu Arg Leu Gly
            180                 185                 190

Arg Ala Met Arg Pro Val Ala Phe Ile Asp Asp Lys Gln Ile Ala
        195                 200                 205

Asn Arg Val Ile Ala Gly Leu Arg Val Tyr Thr Ala Lys His Ile Arg
    210                 215                 220

Gln Met Ile Asp Glu Thr Gly Ala Gln Glu Val Leu Leu Ala Ile Pro
225                 230                 235                 240

Ser Ala Thr Arg Ala Arg Arg Glu Ile Leu Glu Ser Leu Glu Pro
                245                 250                 255

Phe Pro Leu His Val Arg Ser Met Pro Gly Phe Met Asp Leu Ala Ser
            260                 265                 270

Gly Arg Val Lys Val Asp Asp Leu Gln Glu Val Asp Ile Ala Asp Leu
        275                 280                 285

Leu Gly Arg Asp Ser Val Ala Pro Arg Lys Glu Leu Leu Glu Arg Cys
    290                 295                 300

Ile Arg Gly Gln Val Val Met Val Thr Gly Ala Gly Ser Ile Gly
305                 310                 315                 320

Ser Glu Leu Cys Arg Gln Ile Met Ser Cys Ser Pro Ser Val Leu Ile
                325                 330                 335

Leu Phe Glu His Ser Glu Tyr Asn Leu Tyr Ser Ile His Gln Glu Leu
            340                 345                 350

Glu Arg Arg Ile Lys Arg Glu Ser Leu Ser Val Asn Leu Leu Pro Ile
```

```
                355                 360                 365
Leu Gly Ser Val Arg Asn Pro Glu Arg Leu Val Asp Val Met Arg Thr
            370                 375                 380

Trp Lys Val Asn Thr Val Tyr His Ala Ala Tyr Lys His Val Pro
385                 390                 395                 400

Ile Val Glu His Asn Ile Ala Glu Gly Val Leu Asn Asn Val Ile Gly
                405                 410                 415

Thr Leu His Ala Val Gln Ala Val Gln Val Gly Val Gln Asn Phe
            420                 425                 430

Val Leu Ile Ser Thr Asp Lys Ala Val Arg Pro Thr Asn Val Met Gly
            435                 440                 445

Ser Thr Lys Arg Leu Ala Glu Met Val Leu Gln Ala Leu Ser Asn Glu
            450                 455                 460

Ser Ala Pro Val Leu Phe Gly Asp Arg Lys Asp Val His His Val Asn
465                 470                 475                 480

Lys Thr Arg Phe Thr Met Val Arg Phe Gly Asn Val Leu Gly Ser Ser
                485                 490                 495

Gly Ser Val Ile Pro Leu Phe Arg Glu Gln Ile Lys Arg Gly Gly Pro
            500                 505                 510

Val Thr Val Thr His Pro Ser Ile Thr Arg Tyr Phe Met Thr Ile Pro
            515                 520                 525

Glu Ala Ala Gln Leu Val Ile Gln Ala Gly Ser Met Gly Gln Gly Gly
            530                 535                 540

Asp Val Phe Val Leu Asp Met Gly Pro Pro Val Asn Ile Leu Glu Leu
545                 550                 555                 560

Ala Glu Lys Met Ile His Leu Ser Gly Leu Ser Val Arg Ser Glu Arg
                565                 570                 575

Ser Pro His Gly Asp Ile Ala Ile Glu Phe Ser Gly Leu Arg Pro Gly
            580                 585                 590

Glu Lys Leu Tyr Glu Glu Leu Leu Ile Gly Asp Asn Val Asn Pro Thr
            595                 600                 605

Asp His Pro Met Ile Met Arg Ala Asn Glu Glu His Leu Ser Trp Glu
            610                 615                 620

Ala Phe Lys Val Val Leu Glu Gln Leu Leu Ala Ala Val Glu Lys Asp
625                 630                 635                 640

Asp Tyr Ser Arg Val Arg Gln Leu Leu Arg Glu Ile Val Ser Gly Tyr
                645                 650                 655

Ala Pro Asp Gly Glu Ile Val Asp Trp Ile Tyr Arg Gln Arg Arg Arg
            660                 665                 670

Glu Pro

<210> SEQ ID NO 9
<211> LENGTH: 31
<212> TYPE: DNA
<213> ORGANISM: Artificial Sequence
<220> FEATURE:
<223> OTHER INFORMATION: primer

<400> SEQUENCE: 9
actgtacatg tcaatgccaa atcatcaaaa c                              31

<210> SEQ ID NO 10
<211> LENGTH: 30
<212> TYPE: DNA
<213> ORGANISM: Artificial Sequence
<220> FEATURE:
```

<223> OTHER INFORMATION: primer

<400> SEQUENCE: 10
aagctggatc ctcataataa tttcaacaaa                                          30

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
taatacgact cactatag                                                       18

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
caactgcagt cataataatt tcaacaa                                             27

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
actgtacatg tcgatgttgg ataatttgag g                                        31

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
aatatggatc ctcagggttc tcgccgcctc                                          30

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
actttacatg ttgcgtctgg ccatgcg                                             27

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
aatatggatc ctcagggttc tcgccgcctc                                          30

<210> SEQ ID NO 17
<211> LENGTH: 28
<212> TYPE: DNA
<213> ORGANISM: Artificial Sequence
<220> FEATURE:
<223> OTHER INFORMATION: primer

<400> SEQUENCE: 17
actctacatg ttggataact tgcgtgga                                    28

<210> SEQ ID NO 18
<211> LENGTH: 31
<212> TYPE: DNA
<213> ORGANISM: Artificial Sequence
<220> FEATURE:
<223> OTHER INFORMATION: primer

<400> SEQUENCE: 18
aatatggatc ctcagggttc tcgccgcctc t                                31

<210> SEQ ID NO 19
<211> LENGTH: 31
<212> TYPE: DNA
<213> ORGANISM: Artificial Sequence
<220> FEATURE:
<223> OTHER INFORMATION: primer

<400> SEQUENCE: 19
actgtacatg tcaatgccaa atcatcaaaa c                                31

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
aagctggatc ctcataataa tttcaacaaa                                  30

<210> SEQ ID NO 21
<211> LENGTH: 38
<212> TYPE: DNA
<213> ORGANISM: Artificial Sequence
<220> FEATURE:
<223> OTHER INFORMATION: primer

<400> SEQUENCE: 21
atctcttcga atatgggaca ccaccaccac caccacgg                         38

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22
acttggaatt cagggttctc gccgcctctg gc                               32

<210> SEQ ID NO 23
<211> LENGTH: 26
<212> TYPE: DNA
<213> ORGANISM: Artificial Sequence
<220> FEATURE:
<223> OTHER INFORMATION: primer

```
<400> SEQUENCE: 23
actacatgtc ccaccaccac caccac                                        26

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
taattaagct ttcagggttc tcgccgcctc                                    30
```